(12) United States Patent
Rajagopalan et al.

(10) Patent No.: US 7,888,378 B2
(45) Date of Patent: Feb. 15, 2011

(54) THIADIAZOLE COMPOUNDS AND USES THEREOF

(75) Inventors: Raghavan Rajagopalan, Solon, OH (US); Frederick G. Jacobs, O'Fallon, MO (US); Richard B. Dorshow, St. Louis, MO (US)

(73) Assignee: Mallinckrodt Inc., Hazelwood, MO (US)

( * ) Notice: Subject to any disclaimer, the term of this patent is extended or adjusted under 35 U.S.C. 154(b) by 0 days.

(21) Appl. No.: 12/281,156

(22) PCT Filed: Mar. 2, 2007

(86) PCT No.: PCT/US2007/005491

§ 371 (c)(1),
(2), (4) Date: Aug. 29, 2008

(87) PCT Pub. No.: WO2007/103250

PCT Pub. Date: Sep. 13, 2007

(65) Prior Publication Data

US 2009/0036502 A1  Feb. 5, 2009

Related U.S. Application Data

(60) Provisional application No. 60/778,259, filed on Mar. 2, 2006.

(51) Int. Cl.
*A61K 31/381* (2006.01)
(52) U.S. Cl. .................................................. 514/361
(58) Field of Classification Search ........................ None
See application file for complete search history.

(56) References Cited

U.S. PATENT DOCUMENTS

| | | | | |
|---|---|---|---|---|
| 4,352,809 | A * | 10/1982 | Bondinell et al. | ........... 514/293 |
| 5,395,619 | A | 3/1995 | Zalipsky et al. | |
| 5,631,018 | A | 5/1997 | Zalipsky et al. | |
| 5,714,342 | A | 2/1998 | Komoriya et al. | |
| 6,258,378 | B1 | 7/2001 | Schneider et al. | |
| 6,277,403 | B1 | 8/2001 | Pèrez Mendèz et al. | |
| 6,406,713 | B1 | 6/2002 | Janoff et al. | |
| 6,610,322 | B1 | 8/2003 | Keller et al. | |

FOREIGN PATENT DOCUMENTS

| | | |
|---|---|---|
| EP | 0 780 372 | 6/1997 |
| EP | 1 243 178 | 9/2002 |

OTHER PUBLICATIONS

Limmer, ed. Remington: The Science and Practice of Pharmacy, 2000. University of the Sciences in Philadelphia, Lippincott Williams & Wilkins, 20th Ed., especially pp. 218-220.*
Lieberman et al., ed. Pharmaceutical Dosage Forms: Disperse Systems, 1996, Marcel Dekker, Inc. vol. 2, especially pp. 48 and 52.*
"cancer." MedLine Plus. (2009). Accessed Mar. 17, 2009. <http://www.nlm.nih.gov/medlineplus/cancer.html>.*
Dorwald, F. A. Side Reactions in Organic Synthesis, 2005, Wiley: VCH, Weinheim, preface and Chapter 1.*
Golub et al. "Molecular Classification of Cancer: Class Discovery and Class Prediction by Gene Expression Monitoring." Science (1999), vol. 286, 521-537.*
Lala et al. "Role of nitric oxide in tumor progression: Lessons from experimental tumors." Cancer and Metastasis Reviews (1998), 17(1), 91-106.*
Grubb et al., J. Chem. Soc., Faraday Trans., 1996, vol. 92.*
Zeller et al., Jusats Liabigs, Annalen der Chemie, 1972, 766, pp. 32-44.
Girard et al., J. Med. Chem.., 1989, 33(7), pp. 1566-1571.
Hinatowich et al., "Radiolabeling of Antibodies: A Simple and Efficient Method", Science, 1983, 220, p. 613.
Pelegrin et al., "Photo Immunodiagnostics with Antibody—Flurorescein Conjugates in vitro and in vivo Preclinical Studies", Journal of Cellular Pharmacology, 1992, 3, pp. 141-145.
Achilefu et al., "Novel receptor—Targeted Fluroesent Contrast Agents for In Vivo Imaging of Tumores" Investigative Radiology, 2000, 35, pp. 479-485.
Ballou et al., "Tumor Labeling In Vivo Using Cyanine conjugated Momoclonol Antibodies", Cancer Immunology & Immunotherapy, 1995, 41, pp. 257-263.
Licha et al., "New contrast Agent for Optical Imaging: Acid Cleavable conjugates of Cyanine Dyes with Biomolecules", Biomedical Imaging: Reporters, Dyes & Instrumentation, Proceedings of SPIE, 1999, 3600, pp. 29-35.
*Stealth Liposomes*, Lasic and Martin (Eds), 1995, CRC Press, London, pp. 1-6, 13-62, 93-126, 139-148, 197-210, and 233-244.
Krauss et al., "Zur Photolyse Von 1,2,3-Thiadiazolen-II, Esrstudien Zur Stickstoff-Eliminierung", Tetrahedron, 1971, vol. 27, pp. 3953-3957.

* cited by examiner

*Primary Examiner*—Rebecca L Anderson
*Assistant Examiner*—Alicia L Otton
(74) *Attorney, Agent, or Firm*—Greenlee Sullivan P.C.

(57) ABSTRACT

Thiadiazole compounds, compositions, bioconjugates, and methods for targeting and photoactivation at target sites.

24 Claims, 3 Drawing Sheets

THIADIAZOLE COMPOUNDS AND USES THEREOF

CROSS REFERENCE TO RELATED APPLICATIONS

This application is the National Stage of International Application PCT/US07/05491 to Rajagopalan et al. entitled "Thiadiazole Compounds and Uses Thereof", filed Mar. 2, 2007, which claims the benefit under 35 U.S.C. §119(e) of U.S. Provisional Patent Application No. 60/778,259, filed Mar. 2, 2006, to Rajagopalan et al. entitled "Thiadiazole Compounds and Uses Thereof," which are hereby incorporated by reference in their entireties to the extent not inconsistent with the disclosure herein.

FIELD OF THE INVENTION

This invention relates generally to novel thiadiazole compounds, compositions, and methods.

BACKGROUND

The use of visible and near-infrared (NIR) light in clinical practice is growing rapidly. Compounds absorbing or emitting in the visible, NIR, or long-wavelength (UV-A, >350 nm) region of the electromagnetic spectrum are potentially useful for optical tomographic imaging, endoscopic visualization, and phototherapy. However, a major advantage of biomedical optics lies in its therapeutic potential. Phototherapy has been demonstrated to be a safe and effective procedure for the treatment of various surface lesions, both external and internal. Its efficacy is comparable to that of radiotherapy, but without the harmful radiotoxicity of critical non-target organs.

Phototherapy has been in existence for many centuries and has been used to treat various skin surface ailments. As early as 1400 B.C. in India, plant extracts (psoralens), in combination with sunlight, were used to treat vitiligo. In 1903, Von Tappeiner and Jesionek used eosin as a photosensitizer for the treatment of skin cancer, lupus of the skin, and condylomata of female genitalia. Over the years, the combination of psoralens and ultraviolet A (low-energy) radiation has been used to treat a wide variety of dermatological diseases including psoriasis, parapsoriasis, cutaneous T-cell lymphoma, eczema, vitiligo, areata, and neonatal bilirubinemia. Although the potential of cancer phototherapy has been recognized since early 1900's, systematic studies to demonstrate safety and efficacy began only in 1967 with the treatment of breast carcinoma. Dougherty et al. subsequently conclusively established that long-term cure is possible with photodynamic therapy (PDT). Currently, phototherapeutic methods are also being investigated for the treatment of some cardiovascular disorders such as atherosclerosis and vascular restenosis for the treatment rheumatoid arthritis, and for the treatment of some inflammatory diseases such as Crohn's disease.

Phototherapeutic procedures require photosensitizers (i.e. chromophores) which have high absorptivity. These compounds should preferably be chemically inert, and become activated only upon irradiation with light of an appropriate wavelength. Light-initiated selective tissue injury can be induced when these photosensitizers bind to target tissues, either directly or through attachment to a bioactive carrier. Furthermore, if the photosensitizer is also a chemotherapeutic agent (e.g. anthracycline antitumor agents), then an enhanced therapeutic effect can be attained.

Effective phototherapeutic agents should have the following properties: (a) large molar extinction coefficient; (b) long triplet lifetime; (c) high yield of singlet oxygen and/or other reactive intermediates, viz., free radicals, nitrenes, carbenes, open-shell ionic species such as carbonium ions and the like; (d) efficient energy or electron transfer to cellular components; (e) low tendency to form aggregation in aqueous milieu; (f) efficient and selective targeting of lesions; (g) rapid clearance from blood and non-target tissues; (h) low systemic toxicity; and (i) lack of mutagenicity.

Photosensitizers operate via two distinct pathways, termed Types 1 and 2. The Type 1 mechanism is shown in the following scheme:

After photoexcitation, the Type 1 mechanism involves direct energy or electron transfer from the photosensitizer to the cellular components, thereby causing cell death. After photoexcitation, the Type 2 mechanism involves distinct steps as shown in the following scheme:

In the first step, singlet oxygen is generated by energy transfer from the triplet excited state of the photosensitizer to the oxygen molecules surrounding the tissues. In the second step, collision of singlet oxygen with the tissues promotes tissue damage. In both Type 1 and Type 2 mechanisms, the photoreaction proceeds via the lowest triplet state of the sensitizer. Hence, a relatively long triplet lifetime is required for effective phototherapy. In contrast, for diagnostic imaging purposes, a relatively short triplet lifetime is required to avoid photodamage to the tissue caused by photosensitizers.

The biological basis of tissue injury brought about by tumor phototherapeutic agents has been the subject of intensive study. Various reasonable biochemical mechanisms for tissue damage have been postulated even though the type and number of photosensitizers employed in these studies are relatively small. These biochemical mechanisms are as follows: a) cancer cells upregulate the expression of low density lipoprotein (LDL) receptors, and PDT agents bind to LDL and albumin selectively; (b) porphyrin-like substances are selectively taken up by proliferative neovasculature; (c) tumors often contain an increased number of lipid bodies and are thus able to bind to hydrophobic photosensitizers; (d) a combination of "leaky" tumor vasculature and reduced lymphatic drainage causes porphyrin accumulation; (e) tumor cells may have increased capabilities for phagocytosis or pinocytosis of porphyrin aggregates; (f) tumor associated macrophages may be largely responsible for the concentration of photosensitizers in tumors; and (g) cancer cells may undergo apoptosis induced by photosensitizers. Among these mechanisms, (f) and (g) are the most general and, of these two alternatives, there is a general consensus that (f) is the most likely mechanism by which the phototherapeutic effect of porphyrin-like compounds is induced.

Most of the currently known photosensitizers are commonly referred to as PDT agents, and operate via the Type 2 mechanism. For example, Photofrin II, a hematoporphyrin derivative, was approved by the United States Food and Drug Administration for the treatment of bladder, esophageal, and late-stage lung cancers. However, Photofrin II has been shown to have several drawbacks: low molar absorptivity, ($\epsilon$=3000M$^{-1}$), low singlet oxygen quantum yield ($\phi$=0.1), chemical heterogeneity, aggregation, and prolonged cutaneous photosensitivity. Hence, there has been considerable effort in developing safer and more effective photosensitizers for PDT that exhibit improved light absorbance properties, better clearance, and decreased skin photosensitivity compared to those of Photofrin II. These photosensitizers include monomeric porphyrin derivatives, corrins, cyanines, phthalocyanines, phenothiazines, rhodamines, hypocrellins, and the like. However, these phototherapeutic agents also mainly operate via the Type 2 mechanism.

Surprisingly, there has not been much attention directed at developing Type 1 phototherapeutic agents, despite the fact that the Type 1 mechanism seems inherently more efficient than the Type 2 mechanism. First, unlike Type 2, Type 1 photosensitizers do not require oxygen for causing cellular injury. Second, the Type 1 mechanism involves two steps (photoexcitation and direct energy transfer) whereas the Type 2 mechanism involves three steps (photoexcitation, singlet oxygen generation, and energy transfer). Furthermore, some tumors have hypoxic regions that render the Type 2 mechanism ineffective. In spite of the drawbacks associated with the Type 2 mechanism, however, only a small number of compounds have been developed that operate through the Type 1 mechanism, e.g. anthracyline antitumor agents.

SUMMARY

Thiadiazole compounds, compositions, and methods of the following general formula are disclosed.

Formula I where $R^1$, $R^2$, $R^3$, and $R^4$ are independently selected from hydrogen, $C_1$-$C_{10}$ alkyl, $C_5$-$C_{10}$ aryl, $C_5$-$C_{10}$ heteroaryl, $C_1$-$C_{10}$ acyl, halogen, nitro, cyano, —(CH$_2$)$_a$OR$^5$, —(CH$_2$)$_a$CO$_2$R$^5$, —(CH$_2$)$_a$NR$^5$R$^6$, —NR$^6$COR$^5$, —(CH$_2$)$_a$CONR$^5$R$^6$, —(CH$_2$)$_a$SR$^5$, —(CH$_2$)$_a$SOR$^5$, —(CH$_2$)$_a$SO$_2$R$^5$, —(CH$_2$)$_a$CON(R$^5$)E, —(CH$_2$)$_a$N(R$^5$)COE, —(CH$_2$)$_a$N(R$^5$)CON(R$^6$)E, and —(CH$_2$)$_a$N(R$^5$)CSN(R$^6$)E; or $R^1$ and $R^2$, $R^2$ and $R^3$, or $R^3$ and $R^4$, together with the carbon atoms to which they are attached, independently form alicyclic or heterocyclic structures wherein a combination of $R^1$ and $R^2$, or a combination of $R^2$ and $R^3$, or a combination of $R^3$ and $R^4$ is selected from —(CH$_2$)$_b$X(CH$_2$)$_c$—, —C(R$^7$)=C(R$^8$)—C(R$^9$)=C(R$^{10}$)—, —N=C(R$^7$)—C(R$^8$)=C(R$^9$)—, —C(R$^7$)=N—C(R$^8$)=C(R$^9$)—, —C(R$^7$)=C(R$^8$)—N=C(R$^9$)—, —C(R$^7$)=C(R$^8$)—C(R$^9$)=N—, —C(R$^7$)=C(R$^8$)—N(R$^9$)—, —C(R$^7$)=C(R$^8$)—O—, —C(R$^7$)=C(R$^8$)—S—, —N=C(R$^7$)—N=(R$^8$)—, —N=C(R$^7$)—O—, —N=C(R$^7$)—S—, —(R$^7$)=N—N(R$^8$)—, —C(R$^7$)=N—N(R$^8$)—, —C(R$^7$)=N—O—, —N=N—N(R$^8$)—, —N=N—O—, and —N=N—S—; each of b and c independently varies from 0 to 3; X is selected from —O—, —NR$^{11}$—, —S—, and —SO$_2$—; $R^5$ to $R^{11}$ are independently selected from hydrogen, $C_1$-$C_{10}$ alkyl, $C_5$-$C_{10}$ aryl, $C_1$-$C_{10}$ hydroxyalkyl, $C_1$-$C_{10}$ alkoxyalkyl, $C_5$-$C_{10}$ heteroaryl, $C_1$-$C_{10}$ acyl, halogen, nitro, cyano, —(CH$_2$)$_a$OR$^{12}$, —(CH$_2$)$_a$CO$_2$R$^{12}$, —(CH$_2$)$_a$NR$^{12}$R$^{13}$, —NR$^{13}$COR$^{12}$, —(CH$_2$)$_a$CONR$^{12}$R$^{13}$, —(CH$_2$)$_a$SR$^{12}$, —(CH$_2$)$_a$SOR$^{12}$, —(CH$_2$)$_a$SO$^2$R$^{12}$, —(CH$_2$)$_a$CON(R$^{12}$)E, —(CH$_2$)$_a$N(R$^{12}$)COE, —CH$_2$)$_a$N(R$^{12}$)CON(R$^{13}$)E, and —(CH$_2$)$_a$N(R$^{12}$)CSN(R$^{13}$)E; a varies from 0 to 10; $R^{12}$ and $R^{13}$ are independently selected from hydrogen, $C_1$-$C_{10}$ alkyl, $C_5$-$C_{10}$ aryl, $C_1$-$C_{10}$ hydroxyalkyl, $C_1$-$C_{10}$ alkoxyalkyl, $C_5$-$C_{10}$ heteroaryl, and $C_1$-$C_{10}$ acyl; and each occurrence of E is independently either hydrogen or a targeting moiety that binds to a target.

These and other embodiments of the inventive compounds, compositions, and methods will be apparent in light of the following figures, description, and examples.

DETAILED DESCRIPTION

Thiadiazole compounds, bioconjugates, compositions, and methods using the compounds and bioconjugates in in vitro or in vivo biological procedures are described. In one embodiment of the method, the compounds and bioconjugates operate through a Type 1 mechanism capable of generating reactive intermediates such as free radicals that can result in injury or death to cells when the photochemically active compound is at a target site, such as a tumor or lesion. The compounds absorb radiation in the low-energy ultraviolet (UV-A), visible, or near-infrared (NIR) region of the electromagnetic spectrum, and are useful for photodiagnosis, phototherapy, etc. of tumors, inflammation, and other lesions.

The inventive thiadiazoles are small molecules that can be provided to a targeting entity, which then can be selectively photoactivated. The activated compound operates via a Type 1 mechanism in vitro or in vivo and may be used to ablate lesions, etc. Conjugation of the small molecule to a small peptide or other small molecule carrier generally preserves receptor binding capability.

We have previously disclosed inventive compounds containing azide, sulfenate, and azo groups as photochemical agents for targeted binding in photodiagnosis, phototherapy, and other procedures. Each of azides, sulfenates, and azo molecules undergo photofragmentation to result in nitrenes or free radicals. Nitrenes and free radicals induce cell death. When azides, sulfenates, and azo groups are targeted to a particular tissue of interest, the resulting nitrenes and free radicals induce cell death at the target site.

Thiadiazoles are members of a class of heteroaromatic compounds having a five-membered ring that contains two nitrogen atoms and one sulfur atom. Furthermore, the thiadiazoles may be fused with other carbocyclic or heterocyclic rings to from polycyclic thiadiazoles. Various substituents such as electron donating groups, electron withdrawing groups, lipophilic groups, or hydrophilic groups can be attached at the respective carbon atoms for altering physicochemical and/or biological properties, as known to one skilled in the art. The substituents may also optionally include a targeting group that will selectively bind to a desired tissue or lesion. The target may be a biological receptor, an enzyme, etc. For targeting the compound to a biological site, a targeting group E may be attached, unless the thiadiazole compound itself preferentially accumulates in the target tissue.

The inventive thiadiazoles contain nitrogen, nitrogen, and sulfur in the 1, 2, and 3 positions, respectively. Upon photolysis, 1,2,3-thiadiazoles produce diradicals as shown in FIG. 1, and thus are useful for Type 1 phototherapy.

Figure 1:
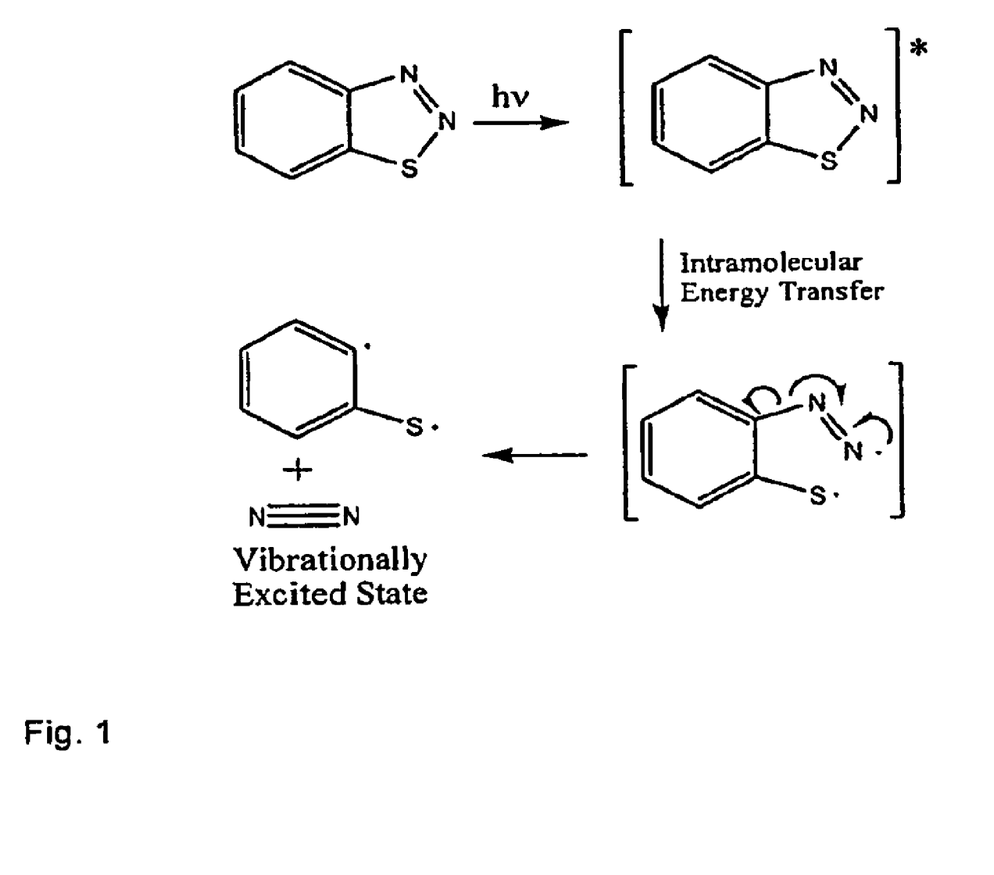
FIG. 1 is a scheme for photoactivation 1,2,3-thiadiazoles.

In the process outlined in FIG. 1, photoexcitation of the aromatic chromophore effects rapid intramolecular energy transfer to the thiadiazole group, resulting in S—N bond rupture with concomitant extrusion of molecular nitrogen and formation of diradicals. The diradicals can also combine with each other to form neutral molecules, provided that their spatial orientation is optimal. However, the diradicals produced by thiadiazoles are 1,3-diradicals that would result in a highly strained cyclopropene ring. To avoid this strain, these diradicals instead react with the environment, i.e. the tissue components, rather than recombine with themselves.

The nitrogen that is released upon photofragmentation is in a vibrationally excited state. Upon relaxation from the excited state, energy in the form of heat is released to the surrounding tissues, with the heat also resulting in tissue damage.

In one embodiment, a bicyclic thiadiazole of Formula I is used

Formula I where $R^1$, $R^2$, $R^3$, and $R^4$ are independently selected from hydrogen, $C_1$-$C_{10}$ alkyl, $C_5$-$C_{10}$ aryl, $C_5$-$C_{10}$ heteroaryl, $C_1$-$C_{10}$ acyl, halogen, nitro, cyano, —$(CH_2)_aOR^5$, —$(CH_2)_aCO_2R^5$, —$(CH_2)_aNR^5R^6$, —$NR^6COR^5$, —$(CH_2)_aCONR^5R^6$, —$(CH_2)_aSR^5$, —$(CH_2)_aSOR^5$, —$(CH_2)_aSO_2R^5$, —$(CH_2)_aCON(R^5)E$, —$(CH_2)_aN(R^5)COE$, —$(CH_2)_aN(R^5)CON(R^6)E$, and —$(CH_2)_aN(R^5)CSN(R^6)E$; or $R^1$ and $R^2$, $R^2$ and $R^3$, or $R^3$ and $R^4$, together with the carbon atoms to which they are attached, independently form alicyclic or heterocyclic structures wherein a combination of $R^1$ and $R^2$, or a combination of $R^2$ and $R^3$, or a combination of $R^3$ and $R^4$ is selected from —$(CH_2)_bX(CH_2)_c$—, —$C(R^7)=C(R^8)$—$C(R^9)=C(R^{10})$—, —$N=C(R^7)$—$C(R^8)=C(R^9)$—, —$C(R^7)=N$—$C(R^8)=C(R^9)$—, —$C(R^7)=C(R^8)$—$N=C(R^9)$—, —$C(R^7)=C(R^8)$—$C(R^9)=N$—, —$C(R^7)=C(R^8)$—$N(R^9)$—, —$C(R^7)=C(R^8)$—O—, —$C(R^7)=C(R^8)$—S—, —$N=C(R^7)$—$N=(R^8)$—, —$N=C(R^7)$—O—, —$N=C(R^7)$—S—, —$(R^7)=N$—$N(R^8)$—, —$C(R^7)=N$—$N(R^9)$—, —$C(R^7)=N$—O—, —$N=N$—$N(R^8)$—, —$N=N$—O—, and —$N=N$—S—; each of b and c independently varies from 0 to 3; X is selected from —O—, —$NR^{11}$—, —S—, and —$SO_2$—; $R^5$ to $R^{11}$ are independently selected from hydrogen, $C_1$-$C_{10}$ alkyl, $C_5$-$C_{10}$ aryl, $C_1$-$C_{10}$ hydroxyalkyl, $C_1$-$C_{10}$ alkoxyalkyl, $C_5$-$C_{10}$ heteroaryl, $C_1$-$C_{10}$ acyl, halogen, nitro, cyano, —$(CH_2)_aOR^{12}$, —$(CH_2)_aCO_2R^{12}$, —$(CH_2)_aNR^{12}R^{13}$, —$NR^{13}COR^{12}$, —$(CH_2)_aCONR^{12}R^{13}$, —$(CH_2)_aSR^{12}$, —$(CH_2)_aSOR^{12}$, —$(CH_2)_aSO^2R^{12}$, —$(CH_2)_aSO_2R^{12}$, —$(CH_2)_aCON(R^{12})E$, —$(CH_2)_aN(R^{12})COE$, —$(CH_2)_aN(R^{12})CON(R^{13})E$, and —$(CH_2)_aN(R^{12})$ CSN($R^{13}$)E; a varies from 0 to 10; $R^{12}$ and $R^{13}$ are independently selected from hydrogen, $C_1$-$C_{10}$ alkyl, $C_5$-$C_{10}$ aryl, $C_1$-$C_{10}$ hydroxyalkyl, $C_1$-$C_{10}$ alkoxyalkyl, $C_5$-$C_{10}$ heteroaryl, and $C_1$-$C_{10}$ acyl; and each occurrence of E, if present, is independently either hydrogen or a targeting moiety that binds to a target.

In another embodiment, Formula I forms a linear tricyclic thiadiazole structure (Formula II)

Formula II wherein $R^2$ and $R^3$ of Formula I are combined to form A and A is selected from —$(CH_2)_bX(CH_2)_c$—, —$C(R^7)=C(R^8)$—$C(R^9)=C(R^{10})$—, —$N=C(R^7)$—$C(R^8)=C(R^9)$—, —$C(R^7)=N$—$C(R^8)=C(R^9)$—, —$(R^7)=C(R^8)$—$N=C(R^9)$—, —$C(R^7)=C(R^8)$—$C(R^9)=N$—, —$C(R^7)=C$ ($R^8$)—$N(R^9)$—, —$C(R^7)=C(R^8)$—O—, —$C(R^7)=C(R^8)$—S—, —$N=C(R^7)$—$N(R^8)$—, —$N=C(R^7)$—O—, —$N=C(R^7)$—S—, —$C(R^7)=N$—$N(R^8)$—, —$C(R^7)=N$—$N(R^8)$, —$C(R^7)=N$—O—, —$N=N$—$N(R^8)$—, —$N=N$—O—, and —$N=N$—S—; each of b and c independently varies from 0 to 3; X is selected from —O—, —$NR^{11}$—, —S—, —SO—, and —$SO_2$—; $R^1$ and $R^4$ may independently be hydrogen, $C_1$-$C_{10}$ alkyl, $C_5$-$C_{10}$ aryl, $C_5$-$C_{10}$ heteroaryl, $C_1$-$C_{10}$ acyl, halogen, nitro, cyano, —$(CH_2)_aOR^5$, —$(CH_2)_aCO_2R^5$, —$(CH_2)_aNR^5R^6$, —$NR^6COR^5$, —$(CH_2)_aCONR^5R^6$, —$(CH_2)_aSR^5$, —$(CH_2)_aSOR^5$, —$(CH_2)_aSO_2R^5$, —$(CH_2)_aCON(R^5)E$, —$(CH_2)_aN(R^5)COE$, —$(CH_2)_aN(R^5)CON(R)E$, and —$(CH_2)_aN(R^5)CSN(R^6)E$; $R^5$ to $R^{11}$ may independently be hydrogen, $C_1$-$C_{10}$ alkyl, $C_5$-$C_{10}$ aryl, $C_1$-$C_{10}$ hydroxyalkyl, $C_1$-$C_{10}$ alkoxyalkyl, $C_5$-$C_{10}$ heteroaryl, $C_1$-$C_{10}$ acyl, halogen, nitro, cyano, —$(CH_2)_aOR^{12}$, —$(CH_2)_aCO_2R^{12}$, —$(CH_2)_aNR^{12}R^{13}$, —$NR^{13}COR^{12}$; —$(CH_2)_aCONR^{12}R^{13}$, —$(CH_2)_aSR^{12}$, —$(CH_2)_aSOR^{12}$, —$(CH_2)_aSO^2R^{12}$, —$(CH_2)_aCON(R^{12})E$, —$(CH_2)_aN(R^{12})COE$, —$(CH_2)_aN$ ($R^{12}$)CON($R^{13}$)E, and —$(CH_2)_aN(R^{12})CSN(R^{13})E$; $R^{12}$ and $R^{13}$ are independently selected from hydrogen, $C_1$-$C_{10}$ alkyl, $C_5$-$C_{10}$ aryl, $C_1$-$C_{10}$ hydroxyalkyl, $C_1$-$C_{10}$ alkoxyalkyl, $C_5$-$C_{10}$ heteroaryl, and $C_1$-$C_{10}$ acyl; where a varies from 0 to 10; and E, if present, is independently either hydrogen or a targeting moiety that binds to a target.

In another embodiment, Formula I forms an angular tricyclic thiadiazole structure (Formula III)

Formula III wherein $R^1$ and $R^2$ of Formula I are combined to form B and B is selected from —$(CH_2)_bX(CH_2)_c$—, —$C(R^7)=C(R^8)$—$C(R^9)=C(R^{10})$—, —$N=C(R^7)$—$C(R^8)=C(R^9)$—, —$C(R^7)=N$—$C(R^8)=C(R^9)$—, —$C(R^7)=C(R^8)$—$N=C$ ($R^9$)—, —$C(R^7)=C(R^8)$—$C(R^9)=N$—, —$C(R^7)=C$ ($R^8$)—$N(R^9)$—, —$C(R^7)=C(R^8)$—O—, —$C(R^7)=C$ $(R^8)$—S—, —N═C($R^7$)—N($R^8$)—, —N═C($R^7$)—O—, —N═C($R^7$)—S—, —C($R^7$)═N—N($R^8$)—, —C($R^7$)═N—N($R^8$)—, —C($R^7$)═N—O—, —N═N—N($R^8$)—, —N═N—O—, and —N═N—S—; each of b and c independently varies from 0 to 3; X is selected from —O—, —NR$^{11}$—, —S—, —SO—, and —SO$_2$—; $R^3$ and $R^4$ may independently be hydrogen, $C_1$-$C_{10}$ alkyl, $C_5$-$C_{10}$ aryl, $C_5$-$C_{10}$ heteroaryl, $C_1$-$C_{10}$ acyl, halogen, nitro, cyano, —(CH$_2$)$_a$OR$^5$, —(CH$_2$)$_a$CO$_2$R$^5$, —(CH$_2$)$_a$NR$^5$R$^6$, —NR$^6$COR$^5$, —(CH$_2$)$_a$CONR$^5$R$^6$, —(CH$_2$)$_a$SR$^5$, —(CH$_2$)$_a$SOR$^5$, —(CH$_2$)$_a$SO$_2$R$^5$, —(CH$_2$)$_a$CON(R$^5$)E, —(CH$_2$)$_a$N(R$^5$)COE, —(CH$_2$)$_a$N(R$^5$)CON(R)E, and —(CH$_2$)$_a$N(R$^5$)CSN(R$^6$)E; $R^5$ to $R^{11}$ may independently be hydrogen, $C_1$-$C_{10}$ alkyl, $C_5$-$C_{10}$ aryl, $C_1$-$C_{10}$ hydroxylakyl, $C_1$-$C_{10}$ alkoxyalkyl, $C_5$-$C_{10}$ heteroaryl, $C_1$-$C_{10}$ acyl, halogen, nitro, cyano, —(CH$_2$)$_a$OR$^{12}$, —(CH$_2$)$_a$CO$_2$R$^{12}$, —(CH$_2$)$_a$NR$^{12}$R$^{13}$, —NR$^{13}$COR$^{12}$; —(CH$_2$)$_a$CONR$^{12}$R$^{13}$, —(CH$_2$)$_a$SR$^{12}$, —(CH$_2$)$_a$SOR$^{12}$, —(CH$_2$)$_a$SO$^2$R$^{12}$, —(CH$_2$)$_a$CON(R$^{12}$)E, —(CH$_2$)$_a$N(R$^{12}$)COE, —(CH$_2$)$_a$N(R$^{12}$)CON(R$^{13}$)E, and —(CH$_2$)$_a$N(R$^{12}$)CSN(R$^{13}$)E; $R^{12}$ and $R^{13}$ are independently selected from hydrogen, $C_1$-$C_{10}$ alkyl, $C_5$-$C_{10}$ aryl, $C_1$-$C_{10}$ hydroxylakyl, $C_1$-$C_{10}$ alkoxyalkyl, $C_5$-$C_{10}$ heteroaryl, and $C_1$-$C_{10}$ acyl; where a varies from 0 to 10; and E, if present, is independently either hydrogen or a targeting moiety that binds to a target.

In another embodiment, Formula I forms an angular tricyclic thiadiazole structure Formula IV)

Formula IV wherein R3 and R4 of Formula 1 are combined to form D and D is selected from —(CH$_2$)$_b$X(CH$_2$)$_c$—, —C(R$^7$)═C(R$^8$)—C(R$^9$)═C(R$^{10}$)—N═C(R$^7$)—C(R$^8$)═C(R$^9$)—, —C(R$^7$)═N—C(R$^8$)═C(R$^9$)—, —C(R$^7$)═C(R$^8$)—N═C(R$^9$)—, —C(R$^7$)═C(R$^8$)—C(R$^9$)═N—, —C(R$^7$)═C(R$^8$)—N (R$^9$)—, —C(R$^7$)═C(R$^8$)—O—, —C(R$^7$)═C(R$^8$)—S—, —N═C(R$^7$)—N(R$^8$)—, —N═C(R$^7$)—O—, —N═C(R$^7$)—S—, —C(R$^7$)═N—N(R$^8$)—, —C(R$^7$)═N—N(R$^8$)—, —C(R$^7$)═N—O—, —N═N—N(R$^8$)—, —N═N—O—, and —N═N—S—; each of b and c independently varies from 0 to 3; X is selected from —O—, —NR$^{11}$—, —S—, —SO—, and —SO$_2$—; R$^1$ and R$^2$ may independently be hydrogen, $C_1$-$C_{10}$ alkyl, $C_5$-$C_{10}$ aryl, $C_5$-$C_{10}$ heteroaryl, $C_1$-$C_{10}$ acyl, halogen, nitro, cyano, —(CH$_2$)$_a$OR$^5$, —(CH$_2$)$_a$CO$_2$R$^5$, —(CH$_2$)$_a$NR$^5$R$^6$, —NR$^6$COR$^5$, —(CH$_2$)$_a$CONR$^5$R$^6$, —(CH$_2$)$_a$SR$^5$, —(CH$_2$)$_a$SOR$^5$, —(CH$_2$)$_a$SO$_2$R$^5$, —(CH$_2$)$_a$CON(R$^5$)E, —(CH$_2$)$_a$N(R$^5$)COE, (CH$_2$)$_a$N(R$^5$)CON(R)E, and —(CH$_2$)$_a$N(R$^5$)CSN(R$^6$)E; $R^5$ to $R^{11}$ may independently be hydrogen, $C_1$-$C_{10}$ alkyl, $C_5$-$C_{10}$ aryl, $C_1$-$C_{10}$ hydroxylakyl, $C_1$-$C_{10}$ alkoxyalkyl, $C_5$-$C_{10}$ heteroaryl, $C_1$-$C_{10}$ acyl, halogen, nitro, cyano, —(CH$_2$)$_a$OR$^{12}$, —(CH$_2$)$_a$CO$_2$R$^{12}$, —(CH$_2$)$_a$NR$^{12}$R$^{13}$, —NR$^{13}$COR$^{12}$; —(CH$_2$)$_a$CONR$^{12}$R$^{13}$, —(CH$_2$)$_a$SR$^{12}$, —(CH$_2$)$_a$SOR$^{12}$, —(CH$_2$)$_a$SO$^2$R$^{12}$, —(CH$_2$)$_a$CON(R$^{12}$)E, —(CH$_2$)$_a$N(R$^{12}$)COE, —(CH$_2$)$_a$N (R$^{12}$)CON(R$^{13}$)E, and —(CH$_2$)$_a$N(R$^{12}$)CSN(R$^{13}$)E; $R^{12}$ and $R^{13}$ are independently selected from hydrogen, $C_1$-$C_{10}$ alkyl, $C_5$-$C_{10}$ aryl, $C_1$-$C_{10}$ hydroxylakyl, $C_1$-$C_{10}$ alkoxyalkyl, $C_5$-$C_{10}$ heteroaryl, and $C_1$-$C_{10}$ acyl; where a varies from 0 to 10; and E, if present, is independently either hydrogen or a targeting moiety that binds to a target.

In another embodiment, Formula I forms a linear tricyclic thiadiazole structure (Formula V)

Formula V wherein $R^2$ and $R^3$ of Formula I are combined to form A and A is —(CH$_2$)$_b$X(CH$_2$)$_c$—; where b is 2 and c is 1; $R^4$ is hydrogen; $R^1$ may independently be hydrogen, $C_1$-$C_{10}$ alkyl, $C_5$-$C_{10}$ aryl, $C_5$-$C_{10}$ heteroaryl, $C_1$-$C_{10}$ acyl, halogen, nitro, cyano, —(CH$_2$)$_a$OR$^5$, —(CH$_2$)$_a$CO$_2$R$^5$, —(CH$_2$)$_a$NR$^5$R$^6$, —NR$^6$COR$^5$; —(CH$_2$)$_a$CONR$^5$R$^6$, —(CH$_2$)$_a$SR$^5$, —(CH$_2$)$_a$SOR$^5$, —(CH$_2$)$_a$SO$_2$R$^5$, —(CH$_2$)$_a$CON(R$^5$)E, —(CH$_2$)$_a$N(R$^5$)COE, —(CH$_2$)$_a$N(R$^5$)CON(R$^6$)E, and —(CH$_2$)$_a$N(R$^5$)CSN(R$^6$)E; where a is 0 to 10; X is —NR$^{11}$—; $R^5$, $R^6$, and $R^{11}$ may independently be hydrogen, $C_1$-$C_{10}$ alkyl, $C_5$-$C_{10}$ aryl, $C_1$-$C_{10}$ hydroxylakyl, and $C_1$-$C_{10}$ alkoxyalkyl; and E, if present, is independently either hydrogen or a targeting moiety that binds to a target. In some cases, a may be 0, 1, 2, 3, 4 5, or 6. For example, in some cases, a may be 0, 1, 2 or 3. As another example, a may simply be either 0 or 1 in some cases.

Figure 2:
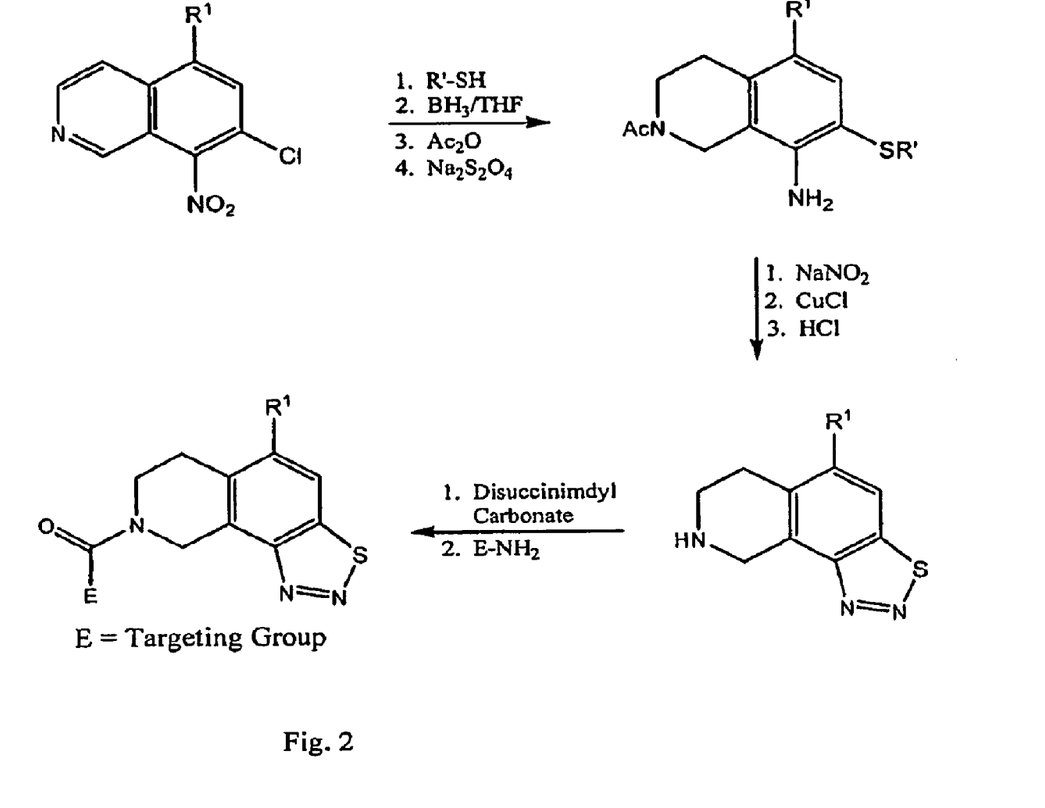
FIG. 2 is a scheme for synthesis of 1,2,3-thiadiazoles.

The general synthesis of thiadiazole can be prepared by methods well known in the art, as illustrated in FIG. 2. The particular thiadiazole derivative of Formula V of the present invention can be prepared as described in Zeller et al. Jusuts Liebigs. Annalen der Chemie 1972, 766, 32 and Girard et al. J. Med. Chem. 1989, 32, 1566 each of which is expressly incorporated by reference herein in its entirety. The key-step of the synthesis was the construction of the 1,2,3-thiadiazole ring by oxidative cyclization of anilines (the Hertz reaction: Heustis et al. J. Org. Chem. 1965, 30, 2763) or ortho-alkylthio-substituted diazonium salts.

Figure 3:
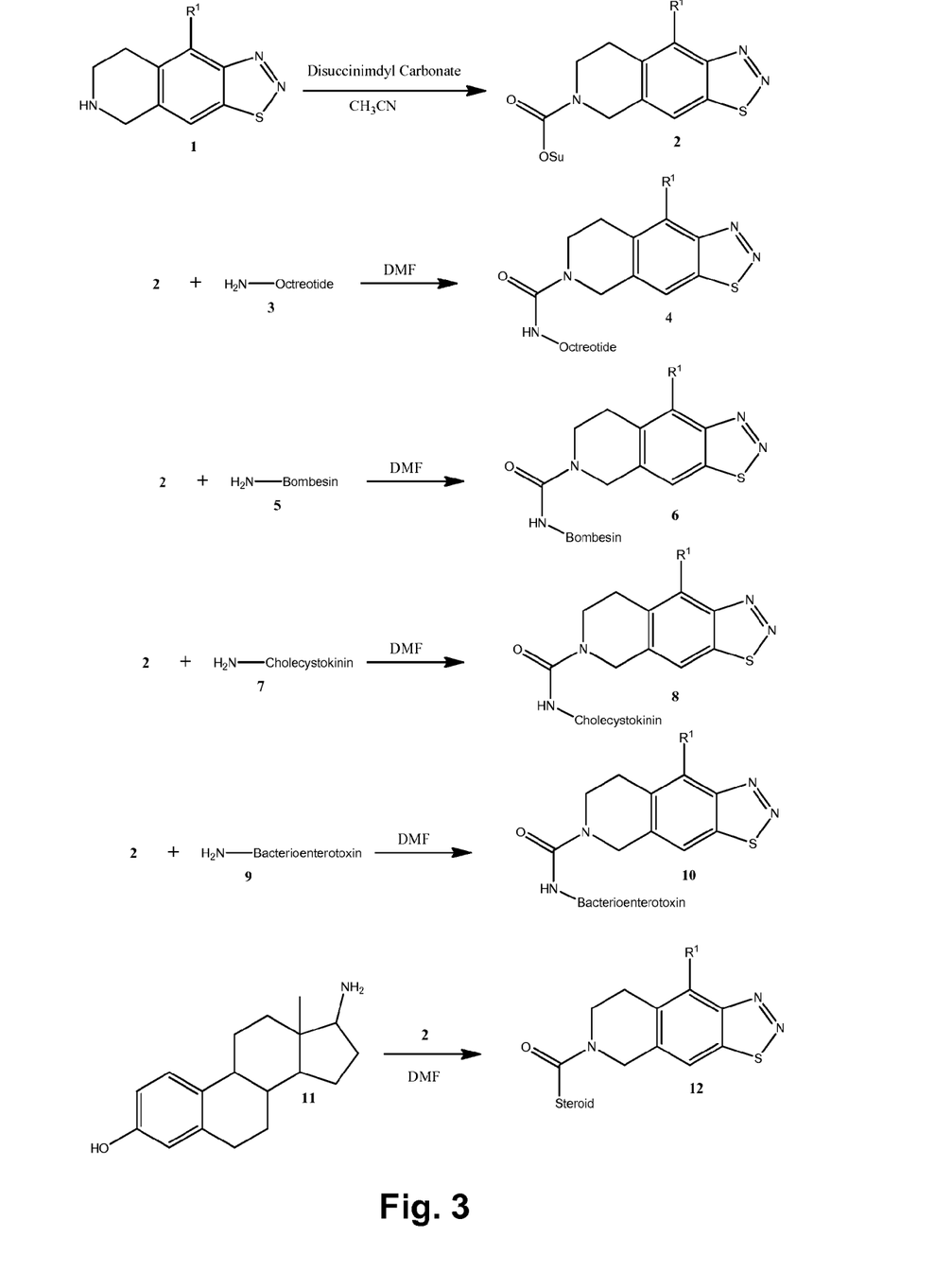
FIG. 3 is a scheme for synthesis of 1,2,3-thiadiazole bioconjugates.

Coupling a targeting group to the thiadiazole is accomplished by methods known in the art, as disclosed in Hnatowich et al., *Radiolabeling of Antibodies: A simple and efficient method, Science,* 1983, 220, p. 613; Pelegrin et al., *Photoimmunodiagnostics with antibody-fluorescein conjugates: in vitro and in vivo preclinical studies, Journal of Cellular Pharmacology* 1992, 3, pp. 141-145; and U.S. Pat. No. 5,714,342, each of which is expressly incorporated by reference herein in its entirety. The coupling of biomolecules such as somatostatin, bombesin, cholecystokinin, bacterioenterotoxin, steroids, and the like to thiadiazoles can be achieved by the use of succinimido active esters as illustrated in FIG. 3. For example, a thiadiazole containing a carboxyl group is activated by making a mixed anhydride in situ with isobutylchloroformate, and then reacted with any biomolecule bearing an amino group. Alternatively, the carboxyl group can be esterified with N-hydroxysuccinimide, and reacted with the amino group to form the amide.

For targeting purposes, an external attachment of a targeting moiety is usually used unless the thiadiazole compounds themselves preferentially accumulate in the target tissue, thereby obviating the need for an additional binding group. For example, administering delta-aminolevulinic acid, an intermediate in porphyrin biosynthesis, results in a two-fold uptake of porphyrins in tumors compared to normal tissues.

Similarly, administering dihydroxyindole-2-carboxylic acid, an intermediate in melanin biosynthesis, produces substantially enhanced levels of melanin in melanoma cells compared to normal cells. Thus, the inventive compound may be delivered to the site of a lesion by attaching it to these types of biosynthetic intermediates. Thus, E may be absent, or may be hydrogen or another group, or may be a targeting moiety. A targeting moiety includes but is not limited to one or more specific sites of a molecule which will bind to a particular complementary site, such as the specific sequence of amino acids in a region of an antibody that binds to the specific antigen binding site. E may be all or a portion of an antibody (monoclonal or polyclonal), peptide, peptidomimetic, carbohydrate, glycomimetic, drug, hormone, nucleic acid, lipid, albumin, receptor binding molecule, inclusion compound such as cyclodextrins, etc. As used in the present invention, the targeting moiety is not limited to a particular sequence or site, but includes anything that will target the inventive compound and/or composition to a particular anatomical and/or physiological site. Examples of compounds that may be used as a targeting moiety for E include, but are not limited to, whole receptor binding compounds or fragments of receptor binding compounds.

In in vitro or in vivo biological systems, including when administered to a mammal, the inventive compounds operate through the Type 1 mechanism. As previously described, there is an intramolecular energy transfer from the photosensitizing unit, viz., the aromatic moiety, to the thiadiazole unit that results in N—S bond rupture followed by nitrogen extrusion and production of two free radicals.

In one example, the targeting moiety of the inventive compound may contain all or part of a steroid hormone or a steroid receptor binding compound, and therefore target steroid hormone sensitive receptors. In this example, the compound is administered, targets the desired site such as breast and/or prostate lesion, is photoactivated, and forms free radicals at this site thereby effecting cell injury or death at the desired target site. Similar target binding compounds and uses will be recognized by one skilled in the art. For example, the targeting group may be a compound that targets and binds to a somatostatin, bombesin, CCK, and/or neurotensin receptor binding molecule, or may be a carcinogenic embryonic antigen-binding compound that binds to a carcinogenic embryonic antigen. These are then photoactivated for radical formation at, for example, lung cancer cells with CCK receptor binding compounds, colorectal cancer cells with ST receptor and carcinoembryonic antigen (CEA) binding compounds, melanoma cells with dihyroxyindolecarboxylic acid, vascular sites of atherosclerotic plaque with integrin receptor binding compounds, brain lesions with amyloid plaque binding molecules, etc.

Successful specific targeting of fluorescent dyes to tumors using antibodies and peptides for diagnostic imaging of tumors has been demonstrated by us and others as described in Achilefu et al., *Novel receptor-targeted fluorescent contrast agents for in viva imaging of tumors, Investigative Radiology,* 2000, 35, pp. 479-485; Ballou et al., *Tumor labeling in vivo using cyanine conjugated monoclonal antibodies, Cancer Immunology and Immunotherapy,* 1995, 41, pp. 257-263; and Licha et al., *New contrast agent for optical imaging: acid cleavable conjugates of cyanine dyes with biomolecules,* in *Biomedical Imaging: Reporters, Dyes and Instrumentation, Proceedings of SPIE,* 1999, 3600, pp. 29-35, each of which is expressly incorporated by reference herein in its entirety. Therefore, receptor-targeted photochemicals are effective in reaching and activation at the site of various lesions.

Methods of performing photochemical procedures using the inventive compounds and compositions are also disclosed. One embodiment administers to a target tissue in an animal an effective amount of a compound having the formula E-L-Ar in a biocompatible composition; and photoactivates the compound by exposing the target tissue to electromagnetic radiation having a wavelength between about 300 nm and about 950 nm; wherein Ar is a bicyclic or tricyclic thiadiazole as in Formulas I, II III, IV, or V, E, if present, is either hydrogen or a targeting moiety that binds to a target, and L is a single bond or a linking moiety that does not substantially reduce a targeting function of E and does not substantially reduce photosensitivity or photoactivity of Ar.

Specifically, the method encompasses administering to a patient an effective amount of the inventive compositions contained in a biologically acceptable formulation. The composition is activated, either immediately or after allowing an interval for its accumulation at a target site, followed by illumination with light of wavelength 300 to 1200 nm, preferably 350 to 850 nm, at the site of the lesion. If the lesion is on the skin surface, or on a photo-accessible surface other than skin, such as a mucosal surface of the oral cavity, vagina, or nasal cavity, it may be directly illuminated. If the lesion is in or on a cavity, it may be illuminated with an endoscopic catheters equipped with a light source. Such an application may be used, for example, with a lesion in a blood vessel, lung, heart, throat, ear, rectum, bladder, stomach, intestines, or esophagus. For a lesion in an organ, such as liver, brain, prostate, breast, pancreas, etc., a photochemical compound in the tissue can be illuminated using a surgical instrument (forceps, scalpel, etc.) containing or configured with an illumination system. Such instruments are known to one skilled in the art, such as fiber optic instruments available from BioSpec (Moscow, 11991, Russia) for example, TC-I fiber optic tool for photodynamic therapy with fine needle tip for irradiating interstitial tumors. A surgeon performing a procedure is thus able to expose a tumor or other target tissue to light of a desired wavelength, power, and fluence rate during a procedure. The intensity, power, duration of illumination, and the wavelength of the light may vary widely depending on the location and site of the lesions. The fluence rate is preferably, but not always, kept below 200 mW/cm$^2$ to minimize thermal effects. Appropriate power depends on the size, depth, and pathology of the lesion. The inventive compositions have broad clinical utility that includes, but are not limited to, phototherapy of tumors, inflammatory processes, and impaired vasculature.

The particular wavelength required for photoactivation to achieve phototherapy with a specific composition may be determined in a variety of ways. As one example, it may be determined empirically from exposing the synthesized compound to light of varying wavelength and thereafter assaying to determine the extent of tissue damage at a targeted site. It may also be determined based upon the known photoactivation maxima for the particular chromophore. In general, agents that act via a Type 1 mechanism can be activated across a wide wavelength spectrum from about 300 nm to about 950 nm. Thus, activation of a Type 1 component or composition may be achieved using an activation wavelength in this range.

The inventive compositions can be formulated for enteral (oral or rectal), parenteral, topical, or cutaneous administration. Topical or cutaneous delivery may also include aerosols, creams, gels, solutions, etc. The compositions are administered in doses effective to achieve the desired objective. Such doses may vary widely depending upon the particular complex employed, the organs or tissues to be examined, the equipment employed in the clinical procedure, the efficacy of the treatment achieved, and the like. These compositions contain an effective amount of the phototherapeutic agent along with conventional pharmaceutical carriers and excipients appropriate for the type of administration contemplated. These compositions may also include stabilizing agents and skin penetration enhancing agents and also may contain pharmaceutically acceptable buffers, emulsifiers, surfactants, and, optionally, electrolytes such as sodium chloride.

Formulations for enteral administration may vary widely as is well known in the art. In general, such formulations are liquids, which include an effective amount of the composition in an aqueous solution or suspension. Such enteral compositions may optionally include buffers, surfactants, emulsifiers, thixotropic agents, and the like. Compositions for oral administration may also contain flavoring agents and other ingredients for enhancing their organoleptic qualities. A topical application can be formulated as a liquid solution, water/oil emulsion, or suspension of particles, depending on the particular nature of the agent and the type of tissue to be targeted.

If the thiadiazole compound is water soluble, for example, a solution in water may be applied to or into the target tissue. Delivery into and through the skin may be enhanced by using well known methods and agents such as transdermal permeation enhancers, for example, "azone", N-alkylcyclic amides, dimethylsulfoxide, long-chained aliphatic acids ($C_{10}$), etc. If the thiadiazole compound is not water soluble, it may be dissolved in a biocompatible oil (soybean oil, fish oil, vitamin E, linseed oil, vegetable oil, glyceride esters, long-chained fatty esters, etc.) and emulsified with surface-active compounds (vegetable or animal phospholipids; lecithin; long-chained fatty salts and alcohols; Pluronics: polyethylene glycol esters and ethers; etc.) in water to make a topical cream, suspension, water/oil emulsion, water/oil microemulsion, or liposomal suspension to be delivered or applied to the target region. In the case of liposomes, the thiadiazole compound may be attached to or be contained in the lamellar material.

The dose of the compound may vary from about 0.1 mg/kg body weight to about 500 mg/kg body weight. In one embodiment, the dose is in the range of about 0.5 to 2 mg/kg body weight. As one example, for compositions administered parenterally, a sterile aqueous solution or suspension of the photosensitizer may be present in a concentration ranging from about 1 nM to about 0.5 M, typically in a concentration from about 1 µM to about 10 mM.

In general, a formulated thiadiazole compound is administered at a dose or in a concentration that is effective, upon exposure to light, to generate radicals at a target tissue or within a biological medium such that cells at the target tissue are injured or killed. The biological medium is exposed for a period of time to light of a wavelength that is effective to activate the dye which produces type 1 destruction in the target tissue. The concentration of the thiadiazole compound at the target tissue is the outcome of either passive or active uptake processes in the tissue. An example of passive uptake would be where the thiadiazole compound is attached or is contained within a particulate carrier. If the carrier is of an appropriate size, in the range of about 100 nm to about 1000 nm, it will leak into the perfusion boundary of vascular tumors. An example of active uptake would be where a receptor based attachment binds a particular receptor that is expressed on the target tissue. The effective concentration of the thiadiazole thus depends on the nature of the formulation, method of delivery, target tissue, activation method and toxicity to the surrounding normal tissue.

In general, a formulated thiadiazole is administered at a dose or in a concentration that is effective, upon exposure to light, to generate radicals at a target tissue or within a biological medium such that cells at the target tissue are injured or killed. The biological medium is exposed for a period of time to light of a wavelength that is effective to activate the dye that produces type 1 destruction in the target tissue. The concentration of the compound at the target tissue is the outcome of either passive or active uptake processes in the tissue. An example of passive uptake would be where the compound is attached or is contained within a particulate carrier. If the carrier is of an appropriate size, in the range of about 100 nm to about 1000 nm, it will leak into the perfusion boundary of vascular tumors. An example of active uptake would be where a receptor based attachment binds a particular receptor that is expressed on the target tissue. The effective concentration of the compound thus depends on the nature of the formulation, method of delivery, target tissue, activation method and toxicity to the surrounding normal tissue. Formulations for topical delivery may also contain liquid or semisolid excipients to assist in the penetration of the photosensitizer. The compositions may also be delivered in an aerosol spray.

In another embodiment, the agents may be formulated as micelles, liposomes, microcapsules, or other microparticles. These formulations may enhance delivery, localization, target specificity, administration, etc. As one example, a liposome formulation of the inventive compound may be beneficial when the compound does not contain a specific targeting moiety (e.g., when E is hydrogen). As another example, a liposome formulation of the inventive compound may be beneficial when the compound has solubility limitations. Preparation and loading of these are well known in the art.

As one example, liposomes may be prepared from dipalmitoyl phosphatidylcholine (DPPC) or egg phosphatidylcholine (PC) because this lipid has a low heat transition. Liposomes are made using standard procedures as known to one skilled in the art (e.g., Braun-Falco et al., (Eds.), Griesbach Conference, *Liposome Dermatics*, Springer-Verlag, Berlin (1992)). Polycaprolactone, poly(glycolic) acid, poly(lactic) acid, polyanhydride or lipids may be formulated as microspheres. As an illustrative example, the optical agent may be mixed with polyvinyl alcohol (PVA), the mixture then dried and coated with ethylene vinyl acetate, then cooled again with PVA. In a liposome, the optical agent may be within one or both lipid bilayers, in the aqueous between the bilayers, or with the center or core. Liposomes may be modified with other molecules and lipids to form a cationic liposome. Liposomes may also be modified with lipids to render their surface more hydrophilic which increases their circulation time in the bloodstream. The thus-modified liposome has been termed a "stealth" liposome, or a long-lived liposome, as described in U.S. Pat. Nos. 6,277,403; 6,610,322; 5,631,018; 5,395,619; and 6,258,378, each of which is expressly incorporated by reference herein in its entirety, and in *Stealth Liposomes, Lasic and Martin* (Eds.) 1995, CRC Press, London, specifically pages 1-6, 13-62, 93-126, 139-148, 197-210, and 233-244. Encapsulation methods include detergent dialysis, freeze drying, film forming, injection, as known to one skilled in the art and disclosed in, for example, U.S. Pat. No. 6,406,713 which is expressly incorporated by reference herein in its entirety.

The thiadiazoles formulated in liposomes, microcapsules, etc. may be administered by any of the routes previously described. In a formulation applied topically, the optical agent is slowly released over time. In an injectable formulation, the liposome capsule circulates in the bloodstream and is delivered to a desired site. The use of liposomes, microcapsules, or other microparticles allows the incorporation of two or more of the inventive compound of different types and capabilities in the composition.

The thiadiazoles could be also used as antimicrobial agents and used for the treatment of infections, wounds, and burn healing, as described by Hamblin et al., in "Targeted photodynamic therapy for infected wounds in mice" in *Optical Methods for Tumor Treatment and Detection: Mechanisms and Techniques in Photodynamic Therapy XI* (Proceedings of SPIE 2002) which is expressly incorporated by reference herein in its entirety. In this regard, the use of liposomes etc., as delivery vehicles for the compounds would be desired.

For example, the thiadiazole may be partially or totally encapsulated in a liposome, microparticle, microcapsule, nanoparticles, or nanocapsule. E may be a hydrogen or a targeting moiety as previously described. The compound is administered to a patient and is localized at an infected site. A phototherapeutic procedure is performed to detect the compound at the infected site and subsequently treat the infected area by activating the compounds to kill the infectious agent.

Example 1

Preparation of 5-chloro-6,7,8,9-tetrahydro[1,2,3]thiadiazolo[5,4-h]isoquinoline

The title compound was prepared in three steps from 8-amino-5-chloroisoquinoline according to the procedure described by Girard et al. *J. Med. Chem.* 1989, 33(7), 1566-1571. The aminoisoquinoline was reacted with sulfur monochloride to give dithiazoloisoquinolinium chloride, which was then treated with 50% sulfuric acid to give 5-chloro[1,2,3]thiadiazolo[5,4-h]isoquinoline. Reduction of this isoquinoline derivative with sodium cyanoborohydride in acetic acid gave the desired thiadiazolotetrahydroisoquinoline derivative.

It should be understood that the embodiments of the present invention shown and described in the specification are only specific embodiments and are not limiting in any way. Therefore, various changes, modifications or alterations to those embodiments may be made or resorted to without departing from the spirit of the invention and the scope of the following claims.

What is claimed is:

1. A method of performing a phototherapy procedure, the method comprising:

administering to a patient an effective amount of a compound of Formula I to a target tissue; and exposing the administered compound at the target tissue to light of wavelength between 300 nm and 1200 nm sufficient to result in injury or death to cells at the target tissue, wherein the target tissue is a tumor or lesion, wherein:

Formula I each of $R^1$, $R^2$, $R^3$, and $R^4$ is independently hydrogen, $C_1$-$C_{10}$ alkyl, $C_5$-$C_{10}$ aryl, $C_5$-$C_{10}$ heteroaryl, $C_1$-$C_{10}$ acyl, halogen, nitro, cyano, —$(CH_2)_aOR^5$, —$(CH_2)_aCO_2R^5$, —$(CH_2)_aNR^5R^6$, —$NR^6COR^5$, —$(CH_2)_aCONR^5R^6$, —$(CH_2)_aSR^5$, —$(CH_2)_aSOR^5$, —$(CH_2)_aSO_2R^5$, —$(CH_2)_aCON(R^5)E$, —$(CH_2)_aN(R^5)COE$, —$(CH_2)_aN(R^5)CON(R^6)E$, or —$(CH_2)_aN(R^5)CSN(R^6)E$; or $R^1$ and $R^2$, $R^2$ and $R^3$, or $R^3$ and $R^4$, together with the carbon atoms to which they are attached, independently form alicyclic or heterocyclic structures, wherein a combination of $R^1$ and $R^2$, or a combination of $R^2$ and $R^3$, or a combination of $R^3$ and $R^4$ is —$(CH_2)_bX(CH_2)_c$—, —$C(R^7)$=$C(R^8)$—$C(R^9)$=$C(R^{10})$—, —$N$=$C(R^7)$—$C(R^8)$=$C(R^9)$—, —$C(R^7)$=$N$—$C(R^8)$=$C(R^9)$—, —$C(R^7)$=$C(R^8)$—$N$=$C(R^9)$—, —$C(R^7)$=$C(R^8)$—$C(R^9)$=$N$—, —$C(R^7)$=$C(R^8)$—$N(R^9)$—, —$C(R^7)$=$C(R^8)$—$O$—, —$C(R^7)$=$C(R^8)$—$S$—, —$N$=$C(R^7)$—$N(R^8)$—, —$N$=$C(R^7)$—$O$—, —$N$=$C(R^7)$—$S$—, —$C(R^7)$=$N$—$N(R^8)$—, —$C(R^7)$=$N$—$N(R^8)$—, —$C(R^7)$=$N$—$O$—, —$N$=$N$—$N(R^8)$—, —$N$=$N$—$O$—, or —$N$=$N$—$S$—;

each of b and c independently varies from 0 to 3;

X is —O—, —$NR^{11}$—, —S—, —SO—, or —$SO_2$—;

each of $R^5$ to $R^{11}$ is independently hydrogen, $C_1$-$C_{10}$ alkyl, $C_5$-$C_{10}$ aryl, $C_1$-$C_{10}$ hydroxyalkyl, $C_1$-$C_{10}$ alkoxyalkyl, $C_5$-$C_{10}$ heteroaryl, $C_1$-$C_{10}$ acyl, halogen, nitro, cyano, —$(CH_2)_aOR^{12}$, —$(CH_2)_aCO_2R^{12}$, —$(CH_2)_aNR^{12}R^{13}$, —$NR^{13}COR^{12}$, —$(CH_2)_aCONR^{12}R^{13}$, —$(CH_2)_aSR^{12}$, —$(CH_2)_aSOR^{12}$, —$(CH_2)_aSO_2R^{12}$, —$(CH_2)_aCON(R^{12})E$, —$(CH_2)_aN(R^{12})COE$, —$(CH_2)_aN(R^{12})CON(R^{13})E$, or —$(CH_2)_aN(R^{12})CSN(R^{13})E$;

a varies from 0 to 10;

each of $R^{12}$ and $R^{13}$ is independently hydrogen, $C_1$-$C_{10}$ alkyl, $C_5$-$C_{10}$ aryl, $C_1$-$C_{10}$ hydroxyalkyl, $C_1$-$C_{10}$ alkoxyalkyl, $C_5$-$C_{10}$ heteroaryl, or $C_1$-$C_{10}$ acyl; and each E is independently hydrogen, a whole or fragmented somatostatin receptor binding molecule, a whole or fragmented ST receptor binding molecule, a whole or fragmented neurotensin receptor binding molecule, a whole or fragmented bombesin receptor binding molecule, a whole or fragmented CCK receptor binding molecule, a whole or fragmented steroid receptor binding molecule, or a whole or fragmented carbohydrate receptor binding molecule.

2. The method of claim 1, the compound being of the following Formula II, wherein:

Formula II

R² and R³ of Formula I are combined to form A, and A is
—(CH₂)ᵦX(CH₂)ᵧ—,  —C(R⁷)=C(R⁸)—C(R⁹)=C(R¹⁰)—,  —N=C(R⁷)—C(R⁸)=C(R⁹)—,  —C(R⁷)=N—C(R⁸)=C(R⁹)—,  —C(R⁷)=C(R⁸)—N=C(R⁹)—, —C(R⁷)=C(R⁸)—C(R⁹)=N—, —C(R⁷)=C(R⁸)—N(R⁹)—, —C(R⁷)=C(R⁸)—O—, —C(R⁷)=C(R⁸)—S—, —N=C(R⁷)—N(R⁸)—, —N=C(R⁷)—O—, —N=C(R⁷)—S—, —C(R⁷)=N—N(R⁸)—, —C(R⁷)=N—N(R⁸)—, —C(R⁷)=N—O—, —N=N—N(R⁸)—, —N=N—O—, or —N=N—S—; and each of R¹ and R⁴ is independently hydrogen, $C_1$-$C_{10}$ alkyl, $C_5$-$C_{10}$ aryl, $C_5$-$C_{10}$ heteroaryl, $C_1$-$C_{10}$ acyl, halogen, nitro, cyano, —(CH₂)ₐOR⁵, —(CH₂)ₐCO₂R⁵, —(CH₂)ₐNR⁵R⁶, —NR⁶COR⁵, —(CH₂)ₐCONR⁵R⁶, —(CH₂)ₐSR⁵, —(CH₂)ₐSOR⁵, —(CH₂)ₐSO₂R⁵, —(CH₂)ₐCON(R⁵)E, —(CH₂)ₐN(R⁵)COE, —(CH₂)ₐN(R⁵)CON(R)E, or —(CH₂)ₐN(R⁵)CSN(R⁶)E.

3. The method of claim 1, the compound being of the following Formula III, wherein:

Formula III

R¹ and R² of Formula I are combined to form B, and B is
—(CH₂)ᵦX(CH₂)ᵧ—,  —C(R⁷)=C(R⁸)—C(R⁹)=C(R¹⁰)—,  —N=C(R⁷)—C(R⁸)=C(R⁹)—,  —C(R⁷)=N—C(R⁸)=C(R⁹)—,  —C(R⁷)=C(R⁸)—N=C(R⁹)—, —C(R⁷)=C(R⁸)—C(R⁹)=N—, —C(R⁷)=C(R⁸)—N(R⁹)—, —C(R⁷)=C(R⁸)—O—, —C(R⁷)=C(R⁸)—S—, —N=C(R⁷)—N(R⁸)—, —N=C(R⁷)—O—, —N=C(R⁷)—S—, —C(R⁷)=N—N(R⁸)—, —C(R⁷)=N—N(R⁸)—, —C(R⁷)=N—O—, —N=N—N(R⁸)—, —N=N—O—, or —N=N—S—; and each of R³ and R⁴ is independently hydrogen, $C_1$-$C_{10}$ alkyl, $C_5$-$C_{10}$ aryl, $C_5$-$C_{10}$ heteroaryl, $C_1$-$C_{10}$ acyl, halogen, nitro, cyano, —(CH₂)ₐOR⁵, —(CH₂)ₐCO₂R⁵, —(CH₂)ₐNR⁵R⁶, —NR⁶COR⁵, —(CH₂)ₐCONR⁵R⁶, —(CH₂)ₐSR⁵, —(CH₂)ₐSOR⁵, —(CH₂)ₐSO₂R⁵, —(CH₂)ₐCON(R⁵)E, —(CH₂)ₐN(R⁵)COE, —(CH₂)ₐN(R⁵)CON(R)E, or —(CH₂)ₐN(R⁵)CSN(R⁶)E.

4. The method of claim 1, the compound being of the following Formula IV, wherein:

Formula IV

R³ and R⁴ of Formula I are combined to form D, and D is
—(CH₂)ᵦX(CH₂)ᵧ—,  —C(R⁷)=C(R⁸)—C(R⁹)=C(R¹⁰)—,  —N=C(R⁷)—C(R⁸)=C(R⁹)—,  —C(R⁷)=N—C(R⁸)=C(R⁹)—,  —C(R⁷)=C(R⁸)—N=C(R⁹)—, —C(R⁷)=C(R⁸)—C(R⁹)=N—, —C(R⁷)=C(R⁸)—N(R⁹)—, —C(R⁷)=C(R⁸)—O—, —C(R⁷)=C(R⁸)—S—, —N=C(R⁷)—N(R⁸)—, —N=C(R⁷)—O—, —N=C(R⁷)—S—, —C(R⁷)=N—N(R⁸)—, —C(R⁷)=N—N(R⁸)—, —C(R⁷)=N—O—, —N=N—N(R⁸)—, —N=N—O—, or —N=N—S—; and each of R¹ and R² is independently hydrogen, $C_1$-$C_{10}$ alkyl, $C_5$-$C_{10}$ aryl, $C_5$-$C_{10}$ heteroaryl, $C_1$-$C_{10}$ acyl, halogen, nitro, cyano, —(CH₂)ₐOR⁵, —(CH₂)ₐCO₂R⁵, —(CH₂)ₐNR⁵R⁶, —NR⁶COR⁵, —(CH₂)ₐCONR⁵R⁶, —(CH₂)ₐSR⁵, —(CH₂)ₐSOR⁵, —(CH₂)ₐSO₂R⁵, —(CH₂)ₐCON(R⁵)E, —(CH₂)ₐN(R⁵)COE, —(CH₂)ₐN(R⁵)CON(R)E, or —(CH₂)ₐN(R⁵)CSN(R⁶)E; and each of R⁵ to R¹¹ is independently hydrogen, $C_1$-$C_{10}$ alkyl, $C_5$-$C_{10}$ aryl, $C_1$-$C_{10}$ hydroxylakyl, $C_1$-$C_{10}$ alkoxyalkyl, $C_5$-$C_{10}$ heteroaryl, $C_1$-$C_{10}$ acyl, halogen, nitro, cyano, —(CH₂)ₐOR¹², —(CH₂)ₐCO₂R¹², —(CH₂)ₐNR¹²R¹³, —NR¹³COR¹², —(CH₂)ₐCONR¹²R¹³, —(CH₂)ₐSR¹², —(CH₂)ₐSOR¹², —(CH₂)ₐSO₂R¹², —(CH₂)ₐCON(R¹²)E, —(CH₂)ₐN(R¹²)COE, —(CH₂)ₐN(R¹²)CON(R¹³)E, or —(CH₂)ₐN(R¹²)CSN(R¹³)E.

5. The method of claim 1, the compound being of the following Formula V, wherein:

Formula V

R² and R³ of Formula I are combined to form A, and A is
—(CH₂)ᵦX(CH₂)ᵧ—;
b is 2, and c is 1;
X is —NR¹¹—;
R⁴ is hydrogen;
R¹ is hydrogen, $C_1$-$C_{10}$ alkyl, $C_5$-$C_{10}$ aryl, $C_5$-$C_{10}$ heteroaryl, $C_1$-$C_{10}$ acyl, halogen, nitro, cyano, —(CH₂)ₐOR⁵, —(CH₂)ₐCO₂R⁵, —(CH₂)ₐNR⁵R⁶, —NR⁶COR⁵, —(CH₂)ₐCONR⁵R⁶, —(CH₂)ₐSR⁵, —(CH₂)ₐSOR⁵, —(CH₂)ₐSO₂R⁵, —(CH₂)ₐCON(R⁵)E, —(CH₂)ₐN(R⁵)COE, —(CH₂)ₐN(R⁵)CON(R⁶)E, or —(CH₂)ₐN(R⁵)CSN(R⁶)E; and each of R⁵, R⁶, and R¹¹ is independently hydrogen, $C_1$-$C_{10}$ alkyl, $C_5$-$C_{10}$ aryl, $C_1$-$C_{10}$ hydroxylakyl, or $C_1$-$C_{10}$ alkoxyalkyl.

6. The method of claim 1, wherein E, if present, is independently selected from whole or fragmented somatostatin receptor binding molecules, whole or fragmented ST receptor binding molecules, whole or fragmented neurotensin receptor binding molecules, whole or fragmented bombesin receptor binding molecules, whole or fragmented CCK receptor binding molecules, whole or fragmented steroid receptor binding molecules, and whole or fragmented carbohydrate receptor binding molecules.

7. The method of claim 1, wherein the compound comprises at least one of an electron donating group, an electron withdrawing group, a lipophilic group, or a hydrophilic group.

8. A method of performing a phototherapy procedure, the method comprising:
administering to a patient a biocompatible composition comprising an effective amount of a compound of Formula I and a biocompatible excipient to a target tissue; and exposing the administered compound at the target tissue to light of wavelength between 300 nm and 1200 nm sufficient to result in injury or death to cells at the target tissue, wherein the target tissue is a tumor or lesion, wherein:

Formula I each of $R^1$, $R^2$, $R^3$, and $R^4$ is independently hydrogen, $C_1$-$C_{10}$ alkyl, $C_5$-$C_{10}$ aryl, $C_5$-$C_{10}$ heteroaryl, $C_1$-$C_{10}$ acyl, halogen, nitro, cyano, —$(CH_2)_aOR^5$, —$(CH_2)_aCO_2R^5$, —$(CH_2)_aNR^5R^6$, —$NR^6COR^5$, —$(CH_2)_aCONR^5R^6$, —$(CH_2)_aSR^5$, —$(CH_2)_aSOR^5$, —$(CH_2)_aSO_2R^5$, —$(CH_2)_aCON(R^5)E$, —$(CH_2)_aN(R^5)COE$, —$(CH_2)_aN(R^5)CON(R^6)E$, or —$(CH_2)_aN(R^5)CSN(R^6)E$; or $R^1$ and $R^2$, $R^2$ and $R^3$, or $R^3$ and $R^4$, together with the carbon atoms to which they are attached, independently form alicyclic or heterocyclic structures, wherein a combination of $R^1$ and $R^2$, or a combination of $R^2$ and $R^3$, or a combination of $R^3$ and $R^4$ is —$(CH_2)_bX(CH_2)_c$—, —$C(R^7)$=$C(R^8)$—$C(R^9)$=$C(R^{10})$—, —N=$C(R^7)$—$C(R^8)$=$C(R^9)$—, —$C(R^7)$=N—$C(R^8)$=$C(R^9)$—, —$C(R^7)$=$C(R^8)$—N=$C(R^9)$—, —$C(R^7)$=$C(R^8)$—$C(R^9)$=N—, —$C(R^7)$=$C(R^8)$—N($R^9$)—, —$C(R^7)$=$C(R^8)$—O—, —$C(R^7)$=$C(R^8)$—S—, —N=$C(R^7)$—N($R^8$)—, —N=$C(R^7)$—O—, —N=$C(R^7)$—S—, —$C(R^7)$=N—N($R^8$)—, —$C(R^7)$=N—N($R^8$)—, —$C(R^7)$=N—O—, —N=N—N($R^8$)—, —N=N—O—, or —N=N—S—;

each of b and c independently varies from 0 to 3;

X is —O—, —$NR^{11}$—, —S—, —SO—, or —$SO_2$—;

each of $R^5$ to $R^{11}$ is independently hydrogen, $C_1$-$C_{10}$ alkyl, $C_5$-$C_{10}$ aryl, $C_1$-$C_{10}$ hydroxyalkyl, $C_1$-$C_{10}$ alkoxyalkyl, $C_5$-$C_{10}$ heteroaryl, $C_1$-$C_{10}$ acyl, halogen, nitro, cyano, —$(CH_2)_aOR^{12}$, —$(CH_2)_aCO_2R^{12}$, —$(CH_2)_aNR^{12}R^{13}$, —$NR^{13}COR^{12}$, —$(CH_2)_aCONR^{12}R^{13}$, —$(CH_2)_aSR^{12}$, —$(CH_2)_aSOR^{12}$, —$(CH_2)_aSO_2R^{12}$, —$(CH_2)_aCON(R^{12})E$, —$(CH_2)_aN(R^{12})COE$, —$(CH_2)_aN(R^{12})CON(R^{13})E$, or —$(CH_2)_aN(R^{12})CSN(R^{13})E$;

a varies from 0 to 10;

each of $R^{12}$ and $R^{13}$ is independently hydrogen, $C_1$-$C_{10}$ alkyl, $C_5$-$C_{10}$ aryl, $C_1$-$C_{10}$ hydroxyalkyl, $C_1$-$C_{10}$ alkoxyalkyl, $C_5$-$C_{10}$ heteroaryl, or $C_1$-$C_{10}$ acyl; and each E is independently hydrogen, a whole or fragmented somatostatin receptor binding molecule, a whole or fragmented ST receptor binding molecule, a whole or fragmented neurotensin receptor binding molecule, a whole or fragmented bombesin receptor binding molecule, a whole or fragmented CCK receptor binding molecule, a whole or fragmented steroid receptor binding molecule, or a whole or fragmented carbohydrate receptor binding molecule.

9. The method of claim 8, wherein the excipient comprises at least one of a buffer, emulsifier, surfactant, or electrolyte.

10. A method of performing a phototherapy procedure, the method comprising:

administering to a patient a biocompatible composition comprising an effective amount of a compound of Formula I and a biocompatible excipient to a target tissue; and exposing the administered compound at the target tissue to light of wavelength between 300 nm and 1200 nm sufficient to result in injury or death to cells at the target tissue, wherein the target tissue is a tumor or lesion, wherein:

Formula I each of $R^1$, $R^2$, $R^3$, and $R^4$ is independently hydrogen, $C_1$-$C_{10}$ alkyl, $C_5$-$C_{10}$ aryl, $C_5$-$C_{10}$ heteroaryl, $C_1$-$C_{10}$ acyl, halogen, nitro, cyano, —$(CH_2)_aOR^5$, —$(CH_2)_aCO_2R^5$, —$(CH_2)_aNR^5R^6$, —$NR^6COR^5$, —$(CH_2)_aCONR^5R^6$, —$(CH_2)_aSR^5$, —$(CH_2)_aSOR^5$, —$(CH_2)_aSO_2R^5$, —$(CH_2)_aCON(R^5)E$, —$(CH_2)_aN(R^5)COE$, —$(CH_2)_aN(R^5)CON(R^6)E$, or —$(CH_2)_aN(R^5)CSN(R^6)E$; or $R^1$ and $R^2$, $R^2$ and $R^3$, or $R^3$ and $R^4$, together with the carbon atoms to which they are attached, independently form alicyclic or heterocyclic structures, wherein a combination of $R^1$ and $R^2$, or a combination of $R^2$ and $R^3$, or a combination of $R^3$ and $R^4$ is —$(CH_2)_bX(CH_2)_c$—, —$C(R^7)$=$C(R^8)$—$C(R^9)$=$C(R^{10})$—, —N=$C(R^7)$—$C(R^8)$=$C(R^9)$—, —$C(R^7)$=N—$C(R^8)$=$C(R^9)$—, —$C(R^7)$=$C(R^8)$—N=$C(R^9)$—, —$C(R^7)$=$C(R^8)$—$C(R^9)$=N—, —$C(R^7)$=$C(R^8)$—N($R^9$)—, —$C(R^7)$=$C(R^8)$—O—, —$C(R^7)$=$C(R^8)$—S—, —N=$C(R^7)$—N($R^8$)—, —N=$C(R^7)$—O—, —N=$C(R^7)$—S—, —$C(R^7)$=N—N($R^8$)—, —$C(R^7)$=N—N($R^8$)—, —$C(R^7)$=N—O—, —N=N—N($R^8$)—, —N=N—O—, or —N=N—S—;

each of b and c independently varies from 0 to 3;

X is —O—, —$NR^{11}$—, —S—, —SO—, or —$SO_2$—;

each of $R^5$ to $R^{11}$ is independently hydrogen, $C_1$-$C_{10}$ alkyl, $C_5$-$C_{10}$ aryl, $C_1$-$C_{10}$ hydroxyalkyl, $C_1$-$C_{10}$ alkoxyalkyl, $C_5$-$C_{10}$ heteroaryl, $C_1$-$C_{10}$ acyl, halogen, nitro, cyano, —$(CH_2)_aOR^{12}$, —$(CH_2)_aCO_2R^{12}$, —$(CH_2)_aNR^{12}R^{13}$, —$NR^{13}COR^{12}$, —$(CH_2)_aCONR^{12}R^{13}$, —$(CH_2)_aSR^{12}$, —$(CH_2)_aSOR^{12}$, —$(CH_2)_aSO_2R^{12}$, —$(CH_2)_aCON(R^{12})E$, —$(CH_2)_aN(R^{12})COE$, —$(CH_2)_aN(R^{12})CON(R^{13})E$, or —$(CH_2)_aN(R^{12})CSN(R^{13})E$;

a varies from 0 to 10;

each of $R^{12}$ and $R^{13}$ is independently hydrogen, $C_1$-$C_{10}$ alkyl, $C_5$-$C_{10}$ aryl, $C_1$-$C_{10}$ hydroxyalkyl, $C_1$-$C_{10}$ alkoxyalkyl, $C_5$-$C_{10}$ heteroaryl, or $C_1$-$C_{10}$ acyl; and each E is independently a whole or fragmented somatostatin receptor binding molecule, a whole or fragmented ST receptor binding molecule, a whole or fragmented neurotensin receptor binding molecule, a whole or fragmented bombesin receptor binding molecule, a whole or fragmented CCK receptor binding molecule, a whole or fragmented steroid receptor binding molecule, or a whole or fragmented carbohydrate receptor binding molecule.

11. The method of claim 2, wherein E, if present, is independently selected from whole or fragmented somatostatin receptor binding molecules, whole or fragmented ST receptor binding molecules, whole or fragmented neurotensin receptor binding molecules, whole or fragmented bombesin receptor binding molecules, whole or fragmented CCK receptor binding molecules, whole or fragmented steroid receptor binding molecules, and whole or fragmented carbohydrate receptor binding molecules.

12. A method of performing a phototherapy procedure, the method comprising:
   administering to a patient a biocompatible composition comprising an effective amount of a compound of Formula II and a biocompatible excipient to a target tissue; and
   exposing the administered compound at the target tissue to light of wavelength between 300 nm and 1200 nm sufficient to result in injury or death to cells at the target tissue, wherein the target tissue is a tumor or lesion, wherein:

Formula II

A is —(CH$_2$)$_b$X(CH$_2$)$_c$—, —C(R$^7$)=C(R$^8$)—C(R$^9$)=C(R$^{10}$)—, —N=C(R$^7$)—C(R$^8$)=C(R$^9$)—, —C(R$^7$)=N—C(R$^8$)=C(R$^9$)—, —C(R$^7$)=C(R$^8$)—N=C(R$^9$)—, —C(R$^7$)=C(R$^8$)—C(R$^9$)=N—, —C(R$^7$)=C(R$^8$)—N(R$^9$)—, —C(R$^7$)=C(R$^8$)—O—, —C(R$^7$)=C(R$^8$)—S—, —N=C(R$^7$)—N(R$^8$)—, —N=C(R$^7$)—O—, —N=C(R$^7$)—S—, —C(R$^7$)=N—N(R$^8$)—, —C(R$^7$)=N—N(R$^8$)—, —C(R$^7$)=N—O—, —N=N—O—, or —N=N—S—;

each of R$^1$ and R$^4$ is independently hydrogen, C$_1$-C$_{10}$ alkyl, C$_5$-C$_{10}$ aryl, C$_5$-C$_{10}$ heteroaryl, C$_1$-C$_{10}$ acyl, halogen, nitro, cyano, —(CH$_2$)$_a$OR$^5$, —(CH$_2$)$_a$CO$_2$R$^5$, —(CH$_2$)$_a$NR$^5$R$^6$, —NR$^6$COR$^5$, —(CH$_2$)$_a$CONR$^5$R$^6$, —(CH$_2$)$_a$SR$^5$, —(CH$_2$)$_a$SOR$^5$, —(CH$_2$)$_a$SO$_2$R$^5$, —(CH$_2$)$_a$CON(R$^5$)E, —(CH$_2$)$_a$N(R$^5$)COE, —(CH$_2$)$_a$N(R$^5$)CON(R)E, or —(CH$_2$)$_a$N(R$^5$)CSNR$^6$)E;

each of b and c independently varies from 0 to 3;

X is —O—, —NR$^{11}$—, —S—, —SO—, or —SO$_2$—;

each of R$^5$ to R$^{11}$ is independently hydrogen, C$_1$-C$_{10}$ alkyl, C$_5$-C$_{10}$ aryl, C$_1$-C$_{10}$ hydroxyalkyl, C$_1$-C$_{10}$ alkoxyalkyl, C$_5$-C$_{10}$ heteroaryl, C$_1$-C$_{10}$ acyl, halogen, nitro, cyano, —(CH$_2$)$_a$OR$^{12}$, —(CH$_2$)$_a$CO$_2$R$^{12}$, —(CH$_2$)$_a$NR$^{12}$R$^{13}$, —NR$^{13}$COR$^{12}$, —(CH$_2$)$_a$CONR$^{12}$R$^{13}$, —(CH$_2$)$_a$SR$^{12}$, —(CH$_2$)$_a$SOR$^{12}$, —(CH$_2$)$_a$SO$_2$R$^{12}$, —(CH$_2$)$_a$CON(R$^{12}$)E, —(CH$_2$)$_a$N(R$^{12}$)COE, —(CH$_2$)$_a$N(R$^{12}$)CON(R$^{13}$)E, or —(CH$_2$)$_a$N(R$^{12}$)CSN(R$^{13}$)E;

a varies from 0 to 10;

each of R$^{12}$ and R$^{13}$ is independently hydrogen, C$_1$-C$_{10}$ alkyl, C$_5$-C$_{10}$ aryl, C$_1$-C$_{10}$ hydroxyalkyl, C$_1$-C$_{10}$ alkoxyalkyl, C$_5$-C$_{10}$ heteroaryl, or C$_1$-C$_{10}$ acyl; and each E is independently a whole or fragmented somatostatin receptor binding molecule, a whole or fragmented ST receptor binding molecule, a whole or fragmented neurotensin receptor binding molecule, a whole or fragmented bombesin receptor binding molecule, a whole or fragmented CCK receptor binding molecule, a whole or fragmented steroid receptor binding molecule, or a whole or fragmented carbohydrate receptor binding molecule.

13. The method of claim 3, wherein E, if present, is independently selected from whole or fragmented somatostatin receptor binding molecules, whole or fragmented ST receptor binding molecules, whole or fragmented neurotensin receptor binding molecules, whole or fragmented bombesin receptor binding molecules, whole or fragmented CCK receptor binding molecules, whole or fragmented steroid receptor binding molecules, and whole or fragmented carbohydrate receptor binding molecules.

14. A method of performing a phototherapy procedure, the method comprising:
   administering to a patient a biocompatible composition comprising an effective amount of a compound of Formula III and a biocompatible excipient to a target tissue; and
   exposing the administered compound at the target tissue to light of wavelength between 300 nm and 1200 nm sufficient to result in injury or death to cells at the target tissue, wherein the target tissue is a tumor or lesion, wherein:

Formula III

B is —(CH$_2$)$_b$X(CH$_2$)$_c$—, —C(R$^7$)=C(R$^8$)—C(R$^9$)=C(R$^{10}$)—, —N=C(R$^7$)—C(R$^8$)=C(R$^9$)—, —C(R$^7$)=N—C(R$^8$)=C(R$^9$)—, —C(R$^7$)=C(R$^8$)—N=C(R$^9$)—, —C(R$^7$)=C(R$^8$)—C(R$^9$)=N—, —C(R$^7$)=C(R$^8$)—N(R$^9$)—, —C(R$^7$)=C(R$^8$)—O—, —C(R$^7$)=C(R$^8$)—S—, —N=C(R$^7$)—N(R$^8$)—, —N=C(R$^7$)—O—, —N=C(R$^7$)—S—, —C(R$^7$)=N—N(R$^8$)—, —C(R$^7$)=N—N(R$^8$)—, —C(R$^7$)=N—O—, —N=N—N(R$^8$)—, —N=N—O—, or —N=N—S—;

each of R$^3$ and R$^4$ is independently hydrogen, C$_1$-C$_{10}$ alkyl, C$_5$-C$_{10}$ aryl, C$_5$-C$_{10}$ heteroaryl, C$_1$-C$_{10}$ acyl, halogen, nitro, cyano, —(CH$_2$)$_a$OR$^5$, —(CH$_2$)$_a$CO$_2$R$^5$, —(CH$_2$)$_a$NR$^5$R$^6$, —NR$^6$COR$^5$, —(CH$_2$)$_a$CONR$^5$R$^6$, —(CH$_2$)$_a$SR$^5$, —(CH$_2$)$_a$SOR$^5$, —(CH$_2$)$_a$SO$_2$R$^5$, —(CH$_2$)$_a$CON(R$^5$)E, —(CH$_2$)$_a$N(R$^5$)COE, —(CH$_2$)$_a$N(R$^5$)CON(R)E, or —(CH$_2$)$_a$N(R$^5$)CSN(R$^6$)E;

each of b and c independently varies from 0 to 3;

X is —O—, —NR$^{11}$—, —S—, —SO—, or —SO$_2$—;

each of R$^5$ to R$^{11}$ is independently hydrogen, C$_1$-C$_{10}$ alkyl, C$_5$-C$_{10}$ aryl, C$_1$-C$_{10}$ hydroxyalkyl, C$_1$-C$_{10}$ alkoxyalkyl, C$_5$-C$_{10}$ heteroaryl, C$_1$-C$_{10}$ acyl, halogen, nitro, cyano, —(CH$_2$)$_a$OR$^{12}$, —(CH$_2$)$_a$CO$_2$R$^{12}$, —(CH$_2$)$_a$NR$^{12}$R$^{13}$, —NR$^{13}$COR$^{12}$, —(CH$_2$)$_a$CONR$^{12}$R$^{13}$, —(CH$_2$)$_a$SR$^{12}$, —(CH$_2$)$_a$SOR$^{12}$, —(CH$_2$)$_a$SO$_2$R$^{12}$, —(CH$_2$)$_a$CON(R$^{12}$)E, —(CH$_2$)$_a$N(R$^{12}$)COE, —(CH$_a$)$_a$N(R$^{12}$)CON(R$^{13}$)E, or —(CH$_2$)$_a$N(R$^{12}$)CSN(R$^{13}$)E;

a varies from 0 to 10;

each of R$^{12}$ and R$^{13}$ is independently hydrogen, C$_1$-C$_{10}$ alkyl, C$_5$-C$_{10}$ aryl, C$_1$-C$_{10}$ hydroxyalkyl, C$_1$-C$_{10}$ alkoxyalkyl, C$_5$-C$_{10}$ heteroaryl, or C$_1$-C$_{10}$ acyl; and each E is independently a whole or fragmented somatostatin receptor binding molecule, a whole or fragmented ST receptor binding molecule, a whole or fragmented neurotensin receptor binding molecule, a whole or fragmented bombesin receptor binding molecule, a whole or fragmented CCK receptor binding molecule, a whole or fragmented steroid receptor binding molecule, or a whole or fragmented carbohydrate receptor binding molecule.

15. The method of claim 4, wherein E, if present, is independently selected from whole or fragmented somatostatin receptor binding molecules, whole or fragmented ST receptor binding molecules, whole or fragmented neurotensin receptor binding molecules, whole or fragmented bombesin receptor binding molecules, whole or fragmented CCK receptor binding molecules, whole or fragmented steroid receptor binding molecules, and whole or fragmented carbohydrate receptor binding molecules.

16. A method of performing a phototherapy procedure, the method comprising:
administering to a patient a biocompatible composition comprising an effective amount of a compound of Formula IV and a biocompatible excipient to a target tissue; and
exposing the administered compound at the target tissue to light of wavelength between 300 nm and 1200 nm sufficient to result in injury or death to cells at the target tissue, wherein the target tissue is a tumor or lesion, wherein:

Formula IV

D is —$(CH_2)_b X(CH_2)_c$—, —$C(R^7)$=$C(R^8)$—$C(R^9)$=$C(R^{10})$—, —$N$=$C(R^7)$—$C(R^8)$=$C(R^9)$—, —$C(R^7)$=$N$—$C(R^8)$=$C(R^9)$—, —$C(R^7)$=$C(R^8)$—$N$=$C(R^9)$—, —$C(R^7)$=$C(R^8)$—$C(R^9)$=$N$—, —$C(R^7)$=$C(R^8)$—$N(R^9)$—, —$C(R^7)$=$C(R^8)$—$O$—, —$C(R^7)$=$C(R^8)$—$S$—, —$N$=$C(R^7)$—$N(R^8)$—, —$N$=$C(R^7)$—$O$—, —$N$=$C(R^7)$—$S$—, —$C(R^7)$=$N$—$N(R^8)$—, —$C(R^7)$=$N$—$N(R^8)$—, —$C(R^7)$=$N$—$O$—, —$N$=$N$—$N(R^8)$—, —$N$=$N$—$O$—, or —$N$=$N$—$S$—;

each of $R^1$ and $R^2$ is independently hydrogen, $C_1$-$C_{10}$ alkyl, $C_5$-$C_{10}$ aryl, $C_5$-$C_{10}$ heteroaryl, $C_1$-$C_{10}$ acyl, halogen, nitro, cyano, —$(CH_2)_a OR^5$, —$(CH_2)_a CO_2 R^5$, —$(CH_2)_a NR^5 R^6$, —$NR^6 COR^5$, —$(CH_2)_a CONR^5 R^6$, —$(CH_2)_a SR^5$, —$(CH_2)_a SOR^5$, —$(CH_2)_a SO_2 R^5$, —$(CH_2)_a CON(R^5)E$, —$(CH_2)_a N(R^5)COE$, —$(CH_2)_a N(R^5)CON(R)E$, or —$(CH_2)_a N(R^5)CSN(R^6)E$;

each of b and c independently varies from 0 to 3;

X is —O—, —S—, —SO—, or each of $R^5$ to $R^{11}$ is independently hydrogen, $C_1$-$C_{10}$ alkyl, $C_5$-$C_{10}$ aryl, $C_1$-$C_{10}$ hydroxylakyl, $C_1$-$C_{10}$ alkoxyalkyl, $C_5$-$C_{10}$ heteroaryl, $C_1$-$C_{10}$ acyl, halogen, nitro, cyano, —$(CH_2)_a OR^{12}$, —$(CH_2)_a CO_2 R^{12}$, —$(CH_2)_a NR^{12} R^{13}$, —$NR^{13} COR^{12}$, —$(CH_2)_a CONR^{12} R^{13}$, —$(CH_2)_a SR^{12}$, —$(CH_2)_a SOR^{12}$, —$(CH_2)_a SO_2 R^{12}$, —$(CH_2)_a CON(R^{12})E$, —$(CH_2)_a N(R^{12})COE$, —$(CH_2)_a N(R^{12})CON(R^{13})E$, or —$(CH_2)_a N(R^{12})CSN(R^{13})E$;

a varies from 0 to 10;

each of $R^{12}$ and $R^{13}$ is independently hydrogen, $C_1$-$C_{10}$ alkyl, $C_5$-$C_{10}$ aryl, $C_1$-$C_{10}$ hydroxyalkyl, $C_1$-$C_{10}$ alkoxyalkyl, $C_5$-$C_{10}$ heteroaryl, or $C_1$-$C_{10}$ acyl; and each E is independently a whole or fragmented somatostatin receptor binding molecule, a whole or fragmented ST receptor binding molecule, a whole or fragmented neurotensin receptor binding molecule, a whole or fragmented bombesin receptor binding molecule, a whole or fragmented CCK receptor binding molecule, a whole or fragmented steroid receptor binding molecule, or a whole or fragmented carbohydrate receptor binding molecule.

17. The method of claim 5, wherein E, if present, is independently selected from whole or fragmented somatostatin receptor binding molecules, whole or fragmented ST receptor binding molecules, whole or fragmented neurotensin receptor binding molecules, whole or fragmented bombesin receptor binding molecules, whole or fragmented CCK receptor binding molecules, whole or fragmented steroid receptor binding molecules, and whole or fragmented carbohydrate receptor binding molecules.

18. A method of performing a phototherapy procedure, the method comprising:
administering to a patient a biocompatible composition comprising an effective amount of a compound of Formula V and a biocompatible excipient to a target tissue; and
exposing the administered compound at the target tissue to light of wavelength between 300 nm and 1200 nm sufficient to result in injury or death to cells at the target tissue, wherein the target tissue is a tumor or lesion, wherein:

Formula V

A is —$(CH_2)_b X(CH_2)_c$—;

b is 2, and c is 1;

X is —$NR^{11}$—;

$R^1$ is hydrogen, $C_1$-$C_{10}$ alkyl, $C_5$-$C_{10}$ aryl, $C_5$-$C_{10}$ heteroaryl, $C_1$-$C_{10}$ acyl, halogen, nitro, cyano, —$(CH_2)_a OR^5$, —$(CH_2)_a CO_2 R^5$, —$(CH_2)_a NR^5 R^6$, —$NR^6 COR^5$, —$(CH_2)_a CONR^5 R^6$, —$(CH_2)_a SR^5$, —$(CH_2)_a SOR^5$, —$(CH_2)_a SO_2 R^5$, —$(CH_2)_a CON(R^5)E$, —$(CH_2)_a N(R^5)COE$, —$(CH_2)_a N(R^5)CON(R^6)E$, or —$(CH_2)_a N(R^5)CSN(R^6)E$;

each of $R^5$, $R^6$, and $R^{11}$ is independently hydrogen, $C_1$-$C_{10}$ alkyl, $C_5$-$C_{10}$ aryl, $C_1$-$C_{10}$ hydroxylakyl, or $C_1$-$C_{10}$ alkoxyalkyl;

a varies from 0 to 10; and each E is independently a whole or fragmented somatostatin receptor binding molecule, a whole or fragmented ST receptor binding molecule, a whole or fragmented neurotensin receptor binding molecule, a whole or fragmented bombesin receptor binding molecule, a whole or fragmented CCK receptor binding molecule, a whole or fragmented steroid receptor binding molecule, or a whole or fragmented carbohydrate receptor binding molecule.

19. The method of claim 1, wherein the target tissue is a melanoma cell, a breast lesion, a prostate lesion, a lung cancer cell, a colorectal cancer cell, an atherosclerotic plaque, a brain lesion, a blood vessel lesion, a lung lesion, a heart lesion, a throat lesion, an ear lesion, a rectal lesion, a bladder lesion, a stomach lesion, an intestinal lesion, an esophagus lesion, a liver lesion, or a pancreatic lesion.

20. The method of claim 1, wherein at least one of $R^1$, $R^2$, $R^3$, and $R^4$ includes E; or wherein at least one of a combination of $R^1$ and $R^2$, a combination of $R^2$ and $R^3$, and a combination of $R^3$ and $R^4$, together with the carbon atoms to which they are attached, independently form an alicyclic or heterocyclic structure that includes E.

21. The method of claim 1, wherein each E is hydrogen.

22. The method of claim 1, wherein each E is a whole or fragmented somatostatin receptor binding molecule, a whole or fragmented ST receptor binding molecule, a whole or fragmented neurotensin receptor binding molecule, a whole or fragmented bombesin receptor binding molecule, or whole or fragmented CCK receptor binding molecule.

23. The method of claim 1, wherein each E is a whole or fragmented steroid receptor binding molecule.

24. The method of claim 1, wherein each E is a whole or fragmented carbohydrate receptor binding molecule.

* * * * *

UNITED STATES PATENT AND TRADEMARK OFFICE
CERTIFICATE OF CORRECTION

PATENT NO.       : 7,888,378 B2
APPLICATION NO.  : 12/281156
DATED            : February 15, 2011
INVENTOR(S)      : Raghavan Rajagopalan et al.

Page 1 of 1

It is certified that error appears in the above-identified patent and that said Letters Patent is hereby corrected as shown below:

In the Specification:

In claim 14, column 20, line 62, please replace "–$(CH_a)_aN(R^{12})CON(R^{13})E$," with -- –$(CH_2)_aN(R^{12})CON(R^{13})E$, --

In claim 16, column 21, line 59, please replace "X is –O–, –S–, –SO–, or" with -- X is –O–, –$NR^{11}$–, –S–, –SO–, or –$SO_2$–; --

Signed and Sealed this
Third Day of May, 2011

David J. Kappos
*Director of the United States Patent and Trademark Office*